(12) United States Patent
Elhawary et al.

(10) Patent No.: US 11,406,289 B2
(45) Date of Patent: *Aug. 9, 2022

(54) SYSTEM AND METHOD FOR MONITORING SAFETY AND PRODUCTIVITY OF PHYSICAL TASKS

(71) Applicant: One Million Metrics Corp., New York, NY (US)

(72) Inventors: Haytham Elhawary, New York, NY (US); Aditya Bansal, White Plains, NY (US); Jeff Doong, Jersey City, NJ (US); Matthew Glazer, Long Beach, NY (US); Evan Roche, New York, NY (US); Mijael Damian, New York, NY (US); Derek Squires, Shirley, NY (US); Marina Teper, New York, NY (US)

(73) Assignee: ONE MILLION METRICS CORP., New York, NY (US)

( * ) Notice: Subject to any disclaimer, the term of this patent is extended or adjusted under 35 U.S.C. 154(b) by 218 days.

This patent is subject to a terminal disclaimer.

(21) Appl. No.: 16/524,737

(22) Filed: Jul. 29, 2019

(65) Prior Publication Data

US 2019/0343429 A1 Nov. 14, 2019

Related U.S. Application Data

(63) Continuation-in-part of application No. 15/594,177, filed on May 12, 2017, now Pat. No. 10,674,965,
(Continued)

(51) Int. Cl.
*A61B 5/11* (2006.01)
*A61B 5/00* (2006.01)
*G06V 40/20* (2022.01)

(52) U.S. Cl.
CPC .......... *A61B 5/1118* (2013.01); *A61B 5/1116* (2013.01); *A61B 5/1126* (2013.01);
(Continued)

(58) Field of Classification Search
None
See application file for complete search history.

(56) References Cited

U.S. PATENT DOCUMENTS 7,457,678 B2   11/2008   Smith et al.
7,698,830 B2    4/2010   Townsend et al.
(Continued)

OTHER PUBLICATIONS

Anonymous: "KINETIC Introduces Wearables Against Lifting Injuries Using Intel Technology", Dec. 14, 2015. URL:https://www.prweb.com/pdfdlownload/13128927.pdf, retrieved from the internet on Aug. 27, 2018.
(Continued)

*Primary Examiner* — Benjamin S Melhus
(74) *Attorney, Agent, or Firm* — Myers Wolin, LLC

(57) ABSTRACT

Methods and systems for monitoring workplace safety and evaluating risks is provided, the method comprising receiving signals from at least one wearable device, identifying portions of the signals corresponding to physical activities, excerpting the portions of the signals corresponding to the physical activities, and calculating risk metrics based on measurements extracted from the excerpted portions of the signals, the risk metric indicative of high risk lifting activities.

24 Claims, 24 Drawing Sheets

Related U.S. Application Data which is a continuation-in-part of application No. 14/660,578, filed on Mar. 17, 2015, now Pat. No. 9,833,197.

(60) Provisional application No. 62/786,597, filed on Dec. 31, 2018, provisional application No. 62/711,488, filed on Jul. 28, 2018, provisional application No. 62/335,070, filed on May 12, 2016, provisional application No. 62/110,630, filed on Feb. 2, 2015, provisional application No. 61/953,934, filed on Mar. 17, 2014.

(52) U.S. Cl.
CPC .......... *A61B 5/6823* (2013.01); *A61B 5/6838* (2013.01); *G06V 40/23* (2022.01)

(56) References Cited

U.S. PATENT DOCUMENTS

| | | |
|---|---|---|
| 7,797,771 B1 | 9/2010 | Bossen et al. |
| 8,149,126 B2 | 4/2012 | Little et al. |
| 8,638,228 B2 | 1/2014 | Amigo et al. |
| 8,712,827 B2 | 4/2014 | Mollicone et al. |
| 8,942,662 B2 | 1/2015 | Pan et al. |
| 2007/0118056 A1* | 5/2007 | Wang .................... A61B 5/1117 600/595 |
| 2007/0250286 A1 | 10/2007 | Duncan et al. |
| 2009/0135009 A1 | 5/2009 | Little et al. |
| 2011/0183305 A1 | 7/2011 | Orbach |
| 2011/0213278 A1 | 9/2011 | Horak et al. |
| 2012/0083676 A1 | 4/2012 | Wolfberg et al. |
| 2013/0103416 A1 | 4/2013 | Amigo et al. |
| 2013/0116602 A1* | 5/2013 | Van Den Heuvel ......................... A61B 5/1126 600/595 |
| 2013/0217352 A1 | 8/2013 | Pan et al. |
| 2013/0237882 A1* | 9/2013 | Niemimaki .............. A61B 5/11 600/595 |
| 2013/0244211 A1 | 9/2013 | Dowling et al. |
| 2013/0331993 A1 | 12/2013 | Detsch et al. |
| 2013/0332098 A1 | 12/2013 | Funk et al. |
| 2014/0135592 A1 | 5/2014 | Ohnemus et al. |
| 2014/0163337 A1 | 6/2014 | Horseman |
| 2014/0266737 A1 | 9/2014 | Caldwell |
| 2014/0317135 A1 | 10/2014 | Stivoric et al. |
| 2014/0347265 A1 | 11/2014 | Amione et al. |
| 2015/0279231 A1* | 10/2015 | Kuo ..................... A61B 5/1124 702/19 |
| 2016/0136882 A1* | 5/2016 | Cobbett ............... A61B 5/0022 156/218 |
| 2016/0166880 A1* | 6/2016 | Nakajima .......... G06Q 10/0639 434/247 |
| 2017/0258374 A1* | 9/2017 | Ly .......................... A61B 5/486 |
| 2018/0125394 A1* | 5/2018 | Sartor .................. A61B 5/7246 |
| 2018/0264320 A1* | 9/2018 | Chang ................... A61B 5/1118 |
| 2019/0076066 A1* | 3/2019 | Ajemba ............. A61B 5/14865 |

OTHER PUBLICATIONS

Klint: "The Internet of Anything: This Wearable Could Keep You From Throwing Out Your Back", Feb. 23, 2015 URL:https://wired.com/2015/02/kinetic-wearable-back-protection/, retrieved from the internet on Aug. 27, 2018.

Kinetic: "Kinetic description—We're building wearable devices to improve industrial worker safety", Feb. 11, 2015 URL:https://www.youtube.com/watch?v=AdrZlg9sU_E, retrieved from the internet on Aug. 27, 2018.

Extend European search report with the European search opinion issued for corresponding European Patent No. 16747074.9 dated Sep. 6, 2018.

International Search Report with Written Opinion issued for corresponding International Application No. PCT/US2016/016062 dated May 26, 2016, pp. 1-6.

The extended European search report with supplementary European search report and the European search opinion issued by the European Patent Office for corresponding European Patent Application No. 17796966.4, dated Nov. 27, 2019.

Communication pursuant to Article 94(3) EPC issued by the European Patent Office for corresponding European Patent Application No. 17796966.4, dated Mar. 1, 2021.

\* cited by examiner

SYSTEM AND METHOD FOR MONITORING SAFETY AND PRODUCTIVITY OF PHYSICAL TASKS

CROSS-REFERENCE TO RELATED APPLICATION

This application claims the benefit of U.S. Provisional Patent Application No. 62/711,488, filed Jul. 28, 2018, and claims the benefit of U.S. Provisional Patent Application No. 62/786,597, filed Dec. 31, 2018, and is a continuation in part of U.S. patent application Ser. No. 15/594,177, filed May 12, 2017 which claims the benefit of U.S. Provisional Patent Application No. 62,335,070, filed May 12, 2016, and is a continuation in part of U.S. patent application Ser. No. 14/660,578, filed Mar. 17, 2015 which claims the benefit of U.S. Provisional Patent Application No. 61/953,934, filed Mar. 17, 2014, and U.S. Provisional Patent Application No. 62/110,630, filed Feb. 2, 2015, the contents of each of which are incorporated by reference herein in its entirety.

FIELD OF THE INVENTION

The systems and methods relate to monitoring workplace safety and productivity and generating recommendations to improve such safety and productivity.

BACKGROUND

In industries that require physical manipulation of objects or people, such as material handling, patient handling, manufacturing, or construction, workers often perform a variety of manual tasks such as lifting loads, moving loads from one location to another, pushing and pulling carts or trolleys, complex assembly and manipulation of components using specific motions and using vibration and impact tools. Often these motions require an intense physical effort, and therefore the repetition of these tasks over time can cause fatigue and injury.

Wearable technology has been used extensively in the consumer space to quantify, for example, the number of steps taken, distance traveled, length and quality of sleep and other metrics, but wearable technology has not been able to consistently evaluate safety metrics in the materials handling industry.

Many risks associated with material handling workers exist, including repetitive stress injuries based on extended physical effort over prolonged periods of time.

Current solutions are mostly limited to physical inspection by specialists, since there is a lack of effective tools to predict when lifting posture is incorrect, or when fatigue results in a risky or dangerous change of posture or non-ergonomic lifting techniques when performing tasks. Typically, specialists inspect the workplace and observe tasks, or review video footage provided by the employer. In either case, inspection is typically performed over only a limited period of time, usually 5-60 minutes. Without effective tools, employers (and workers themselves) have difficulty predicting and preventing injury.

Further, while workers are taught correct material handling techniques, such techniques are not tailored to the strengths of a particular worker. Different workers can do a particular task in multiple ways because of varying body types and abilities. Better monitoring of task performance incorporating information about the particular worker involved may allow for customized training techniques.

Further, there is a lack of productivity measuring tools for individual workers, as it is rarely possible to measure in real-time the number and quality of tasks a specific worker is performing including their speed and variation over time. This information could allow managers to optimize productivity or to devise novel forms of incentives based on productivity.

Finally, tasks are typically divided among the workers based partially on physical ability. However, the physical ability to do a specific task is determined based on visual observation without any detailed insights on the actual motion of a worker's body. Quantifying body motion can help supervisors factor such information into task and shift assignments. Therefore, additional information related to the aspects of task performance that increase injury risk can inform the design of a workplace, design of shifts, and assignment of tasks.

Existing systems for analyzing the safety and productivity of material handling tasks by analyzing motion have limited real-world applications due to inherent limitations.

Motion detection based platforms, such as optical systems using complex cameras and sensors, are expensive and are of limited use in a warehouse setting as they require line of sight which is not always possible in crowded warehouse or factory environments.

Electromagnetic based motion sensor systems produce errors when they are close to ferromagnetic materials often present in industrial settings, are expensive and typically require cabling from sensors to processing units, making their continued use impractical in a warehouse setting.

Existing devices provide very limited motion information and are typically bulky and impractical. Existing systems cannot extract adequate information to fully implement risk models, and typically require manual input of risk variables that cannot be measured by the device alone.

Further, in systems where devices are assigned to users for tracking purposes, the devices are typically stored at an employer facility along with devices associated with or assigned to other workers. It is difficult to ensure that a particular user is using the correct device, and that the device is assigned to that worker.

Further, where workers may be tracked, feedback is not always provided, and where feedback is provided, it is not always immediate or provided in a useful form. Further, feedback may not prevent workers from performing dangerous tasks, even where such feedback is received. For example, a worker may receive a warning that it is dangerous to drive a forklift without a helmet, but such a system may not know when the worker is attempting to drive a forklift or prevent the user from doing so if an attempt is detected.

Further, where worker activities may be used to provide feedback, such systems cannot generate insight into longer term injuries, beyond detecting that a single action is potentially dangerous.

Finally, none of the tracking systems described can leverage the tracking information to improve morale by encouraging and incentivizing safe practices or to reduce costs by incentivizing and confirming practices that reduce insurance premiums.

There is a need for a fully automatable system and method that can monitor physical activity of individual workers and evaluate safety and productivity both for individuals and for a workspace as a whole. There is a further need for a platform that can incorporate such evaluations into recommendations for improving the technique of individual workers and physical characteristics of the workplace environment.

Finally, there is a need for such a platform that can leverage data generated to improve morale, ensure safety, and reduce employer costs.

SUMMARY

A computer based method is provided for indicating risk during physical activities, in which the method receives a first signal from a wearable device generated from dynamic activity of the wearable device over time. The method then identifies, from the first signal, an initiation time for a first physical activity performed by a wearer of the wearable device, and calculates measurements of the wearer for the time period during the first physical activity.

The method then repeats the first steps of the method to identify and calculate measurements for a plurality of additional physical activities. The method then calculates an activity risk metric for each identified physical activity from a risk model based on the measurements of the wearer during the corresponding physical activity. The risk metric is indicative of a risk level for the corresponding physical activity. The method then separately calculates a cumulative risk metric indicative of a risk level from multiple physical activities over time.

Once both the activity risk metric for a given activity and a cumulative risk metric over time are calculated, the method generates an alert only if the cumulative risk metric is above a cumulative risk threshold and the activity risk metric for a most recent physical activity is above an activity risk threshold.

The cumulative risk metric may be for a sliding window of time immediately prior to the calculation of the activity risk metric. The cumulative risk metric may be a risk frequency metric, which would be a measure of the frequency of the activity risk metric being above the activity risk threshold during the sliding window of time. In some embodiments, the cumulative risk metric is a measure of rest periods between instances of the activity risk metric being above the activity risk threshold.

In some alternative embodiments, the cumulative risk metric is a measure of the number of physical activities performed during the sliding window.

In some embodiments, the cumulative risk threshold changes over the course of a day or over a longer period of time.

In some embodiments, the cumulative risk metric is based on kinematic variables including at least one of back bending angle and cumulative trunk loading. The cumulative risk metric may then be based on a time integration of kinematic variables over the window of time. Further, the cumulative risk metric may be based on variables different than those on which the activity risk metric is based.

In some embodiments, the design of a job assigned to the wearer may be modified based on the cumulative risk metric associated with the wearer. As one example, if the cumulative risk metric is above the cumulative risk threshold for a specified amount of time, the design of the job may be modified to require the wearer to utilize assist equipment.

The wearable device utilized in such methods may be worn or mounted at the user's hip, and the measurements calculated include measurements of a user's back inferred from movement of the user's hip detected by the wearable device. Further, movement of the user's hip may be detected by an accelerometer, a gyroscope, and an altimeter.

Also provided are methods for incentivizing risk reduction during physical activities. In such an embodiment, the method may receive a first signal from a wearable device generated from dynamic activity of the wearable device over time and identify an initiation time for a first physical activity of a first category of physical activity performed by a wearer of the wearable device.

Once the initiation time for the first physical activity is detected, the method may calculate measurements of the wearer for a time period during the first physical activity from a first signal segment of the first signal for a time period following the initiation time.

The method may then generate a payment for the wearer at a calculated rate associated with the first category of physical activity, the calculated rate based on a base payment rate modified by a risk score associated with the wearer of the wearable device. Both the risk score and the base payment rate are specific to the first category of physical activity.

Either before or after such payment, the method would calculate an activity risk metric from a risk model based on the measurements of the wearer for the time period during the first physical activity, the risk metric being indicative of a risk level of the execution of the physical activity by the wearer. The results of this calculation would then be used to modify the risk score of the wearer associated with the first category of physical activity.

The method would then be repeated to identify additional physical activities of the first category of physical activity and generate payments at a calculated rate associated with the first category of physical activity for each repetition based on the modified risk score at the time of the payment.

In some embodiments, the identification of the initiation time of the physical activity is directly from the first signal, and is by either the wearable device or by a server in communication with the wearable device. In other embodiments, the identification of the initiation time is by the wearer scanning a code associated with the physical activity. For example, if the physical activity is a lifting activity, the code scanned is on a box to be lifted by the wearer.

In still other embodiments, the identification of the initiation time is by a server in communication with the wearable device, where the category is identified based on a log of activity associated with the wearer and stored at the server.

In some such embodiments, the first category of physical activities is one of several categories of physical activity, each of which is associated with distinct base payment rates and risk scores. Accordingly, a modification of a risk score for a category of physical activity would affect only that risk score, and not the corresponding scores for other categories of physical activities.

In some embodiments, a base risk score is established for the first category of physical activity prior to the first physical activity, and the base risk score is modified upon the calculation of an activity risk metric indicative of a high risk physical activity to reduce the calculated rate for future payments. The risk score is similarly modified upon the calculation of an activity risk metric indicative of a low risk physical activity to increase the calculated rate for future activities.

In some embodiments, a cumulative risk score is also calculated, indicative of a risk level from multiple physical activities over time. In such an embodiment, the a cumulative modification of the risk score may be applied to reduce the calculated rate when the cumulative risk metric is above a cumulative risk threshold, and that modification may be removed when the cumulative risk metric returns below the cumulative risk threshold.

In some embodiments, a bonus payment may be applied to a wearer's account if the cumulative risk metric stays below the cumulative risk threshold for a defined period of time.

Also provided is a method for evaluating results of physical activities of workers. Such a method may comprise receiving a first signal from a wearable device indicative of physical characteristics of the wearable device over time and identifying a plurality of signal segments each corresponding to at least one of several expected categories of physical activities. Each such signal segment may then be correlated with a corresponding category of physical activity.

An activity risk metric is then generated and associated with each signal segment, and a log of physical activity performed by the user wearing the wearable device is generated. The log defines the category of physical activity, the activity risk metric, and the time for each signal segment evaluated.

In some embodiments, the log may comprise a complete record of raw data recorded at the wearable device or a complete record of any calculated angles and metrics generated by the device. In other embodiments, the log may define kinematic variables, temperature, air pressure, and height measurements and changes at the time of the associated signal segment. Similarly, it may further define environmental variables or location drawn from sensors located in the environment in which a corresponding physical activity occurs.

The method may further comprise identifying, in the first signal, an injury to a wearer, and may then provide to an employer a segment of the log corresponding to a time period immediately preceding the injury.

Also provided is a system for assigning a wearable device to a user, the system comprising a plurality of wearable devices to be assigned to a plurality of users and a plurality of docking locations for docking the wearable devices. Each of the docking locations is then provided with an indicator.

Each indicator identifies an assigned identity for the wearable devices docked at the corresponding docking location, and when a wearable device is placed at a particular docking location, the wearable device is reprogrammed to correspond to the identity identified by the corresponding indicator.

In some embodiments, the wearable device is assigned to a user has an indicator programmed to indicate a drop off location to which the device must be returned, and the drop off location is selected by the system from a set of unoccupied locations.

In some embodiments, the assigned identity corresponds to a particular user to whom the corresponding wearable device is assigned.

The assigned identity may take the form of a scannable code such that when a user selects a wearable device, they scan the code with a secondary device, thereby assigning the device to themselves.

Also provided is a method for updating insurance premiums for workers. The method comprises associating a risk score with a worker, receiving a signal from the wearable device generated from dynamic activity of the wearable device over time, and identifying an initiation time for a first physical activity of a first category of physical activity performed by the worker.

The method then defines a signal segment corresponding to the first physical activity and calculates measurements of the worker for the time period during the first physical activity from the signal segment. The method then calculates an activity risk metric from a risk model based on the measurements of the first worker during the time period, the metric being indicative of a risk level of the execution of the physical activity by the worker.

The method then repeats the detection and analysis to identify and evaluate several physical activities. The method then modifies the risk score of the worker based on the activity risk metric calculated and calculates an insurance premium for the worker based on the risk score.

In some embodiments, the worker is a member of a group of workers, and each worker in the group is assigned an independent risk score. The method then calculates and modifies risk scores for each worker and calculates an insurance premium for the group based on the individual risk scores of the workers.

In some embodiments, the method comprises calculating a cumulative risk metric indicative of a risk level from multiple physical activities over time and modifies the risk score of the worker based on the cumulative risk metric.

Typically, the risk score is a predictive metric for predicting whether the group has a high probability of incurring an injury. In some embodiments, the insurance premium may be calculated based at least partially on cumulative baseline risk for a set of tasks performed by the worker.

Also provided is a method for calibrating a wearable device, the method comprising determining that an actual physical posture or physical activity of a user wearing the wearable device corresponds to a known physical posture or physical activity, receiving a first signal from the wearable device generated from dynamic activity of the wearable device over time, identifying a calibration signal segment corresponding to an expected pattern for a calibration activity, and identifying a device location relative to the user based on a variance between the calibration signal segment and the expected pattern. For example, the calibration activity may be walking.

In some embodiments, the device location is a side of the user's body or a height relative to the user's hips. The device location may also be an offset relative to a user's hip indicating that the device is forwards or backwards of the user's hip. If the method determines that the wearable device is improperly positioned, the method may alert the user to the same.

DETAILED DESCRIPTION OF THE PREFERRED EMBODIMENTS

Figure 1:
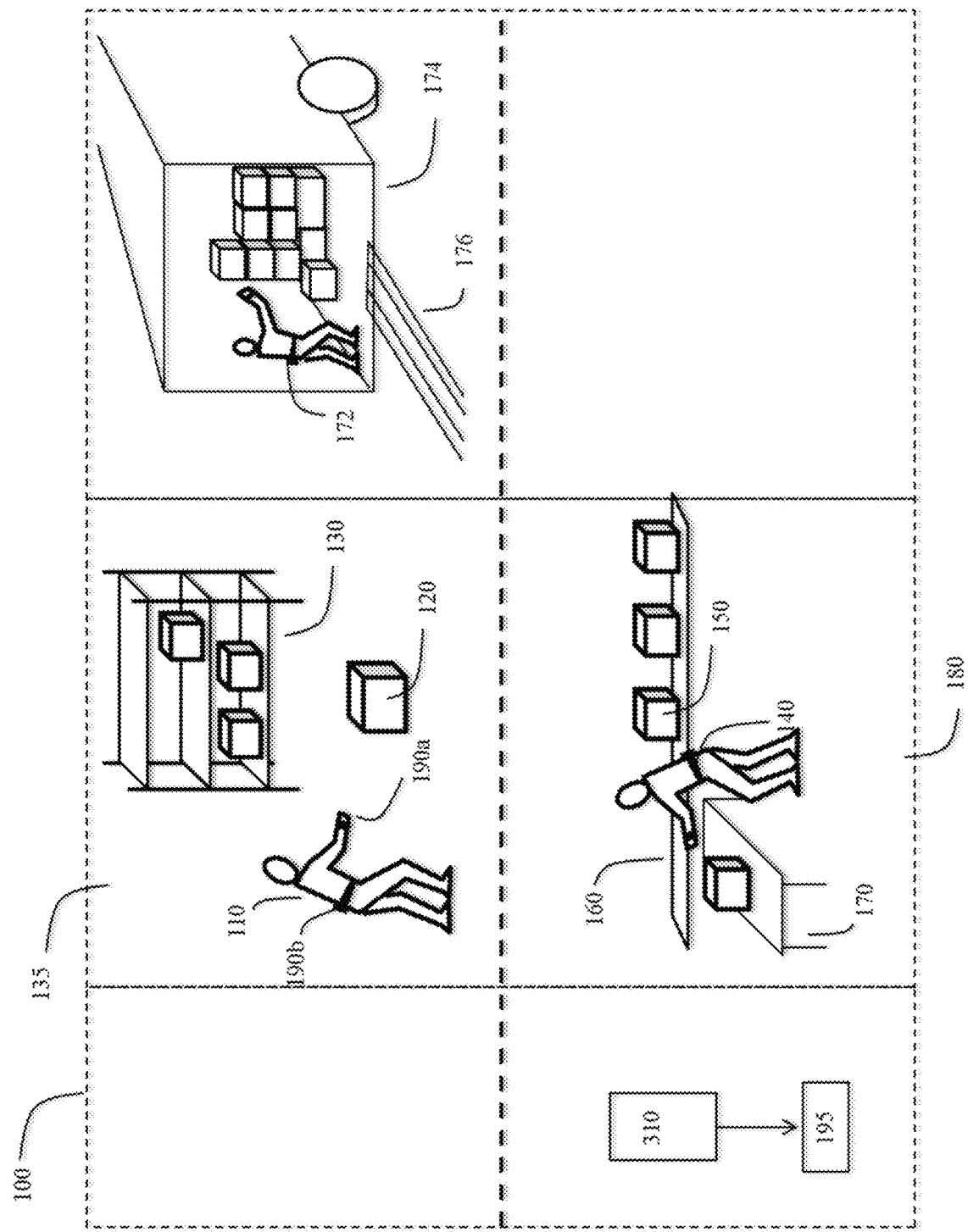
FIG. 1 illustrates a physical environment for implementing a method for monitoring safety.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

This disclosure describes the best mode or modes of practicing the invention as presently contemplated. This description is not intended to be understood in a limiting sense, but provides an example of the invention presented solely for illustrative purposes by reference to the accompanying drawings to advise one of ordinary skill in the art of the advantages and construction of the invention. In the various views of the drawings, like reference characters designate like or similar parts.

Figure 2A:
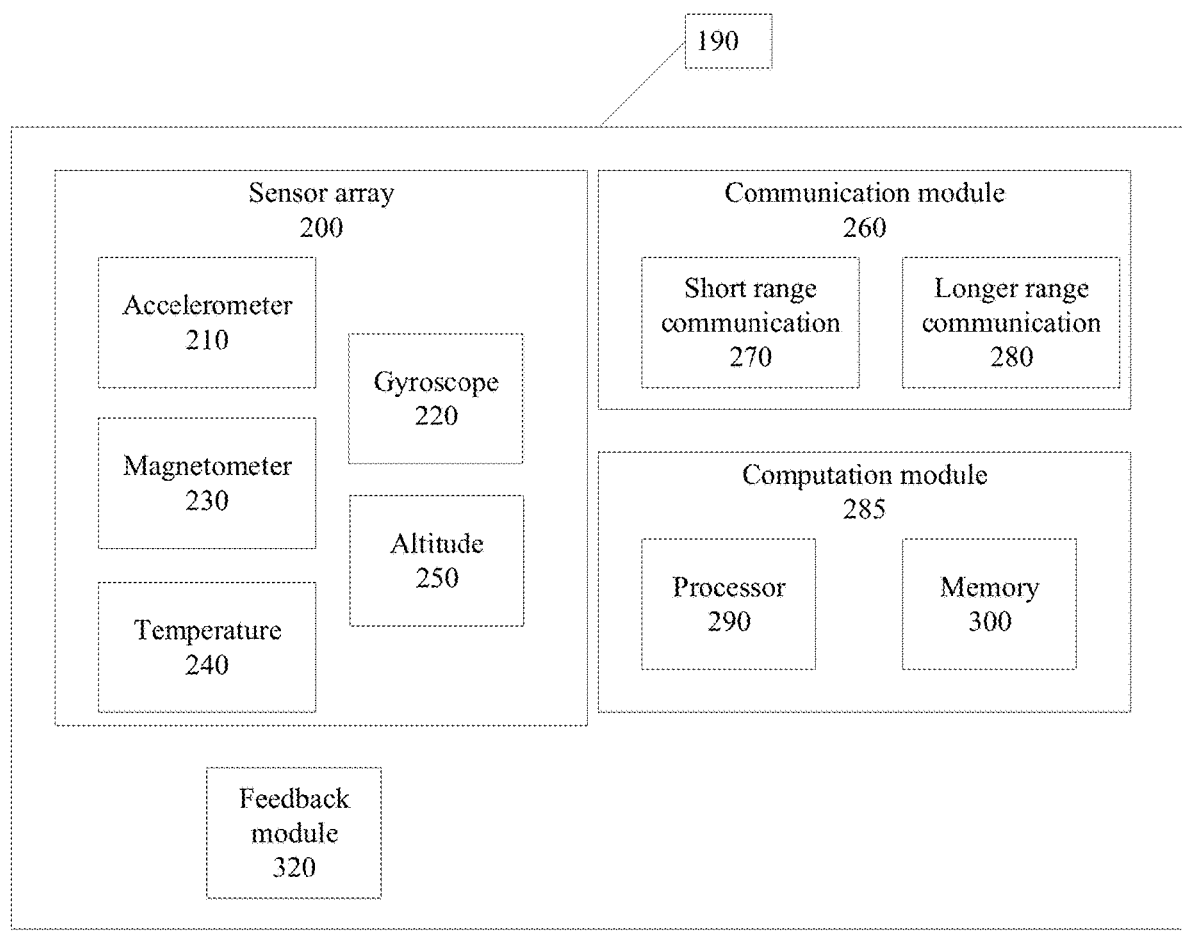
FIG. 2A is a schematic for a sensor and sensor packaging for use in implementing the method.
Figure 2B:
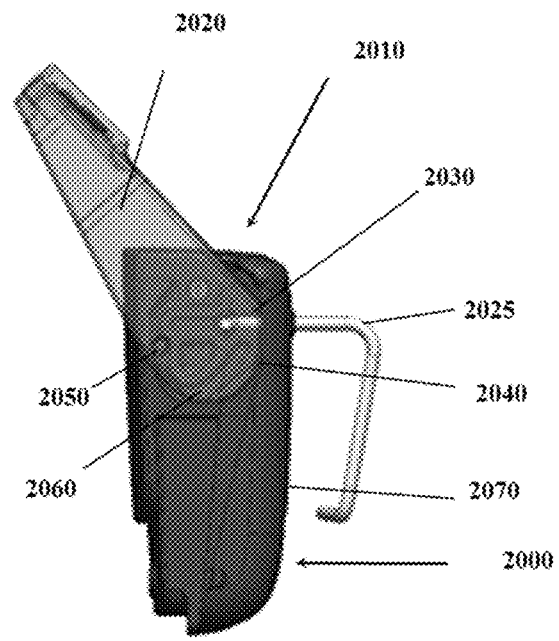
FIGS. 2B-D show a sensor packaging containing a clip for fixing the sensor to a user.
Figure 2C:
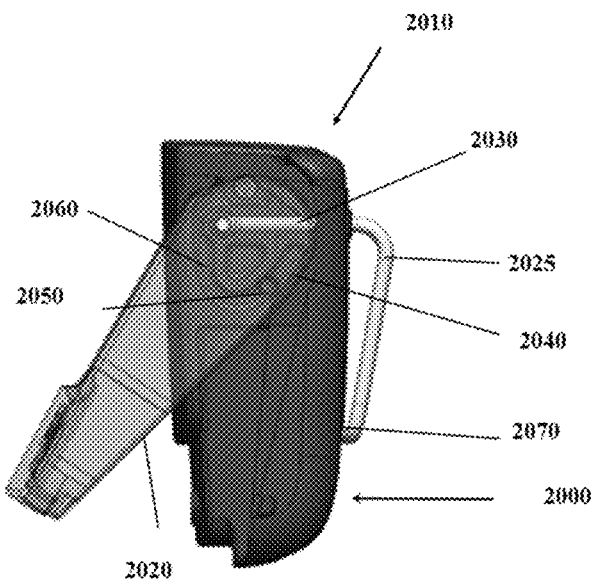
Figure 2D:
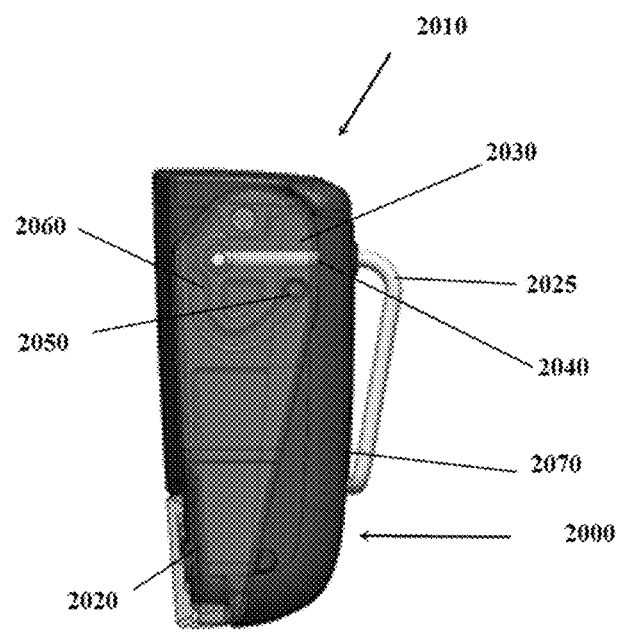
Figure 3A:
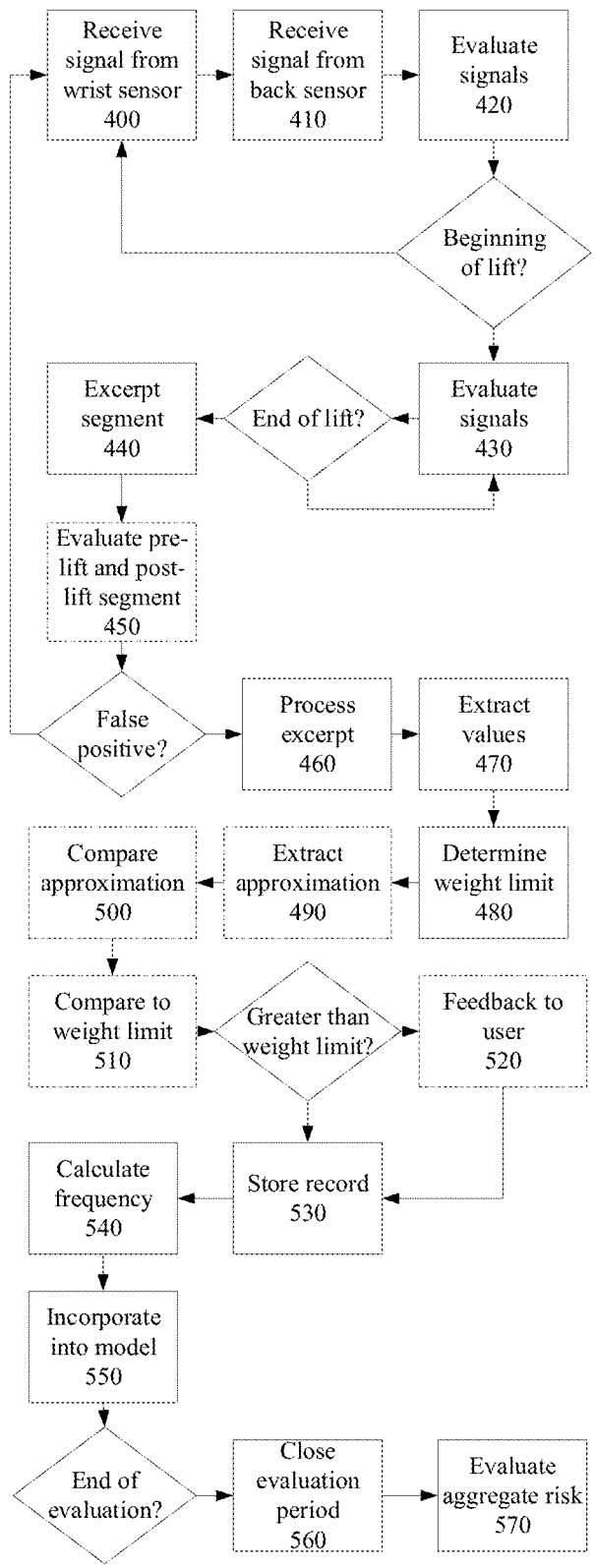
FIG. 3A is a flowchart illustrating a method for monitoring safety.
Figure 3B:
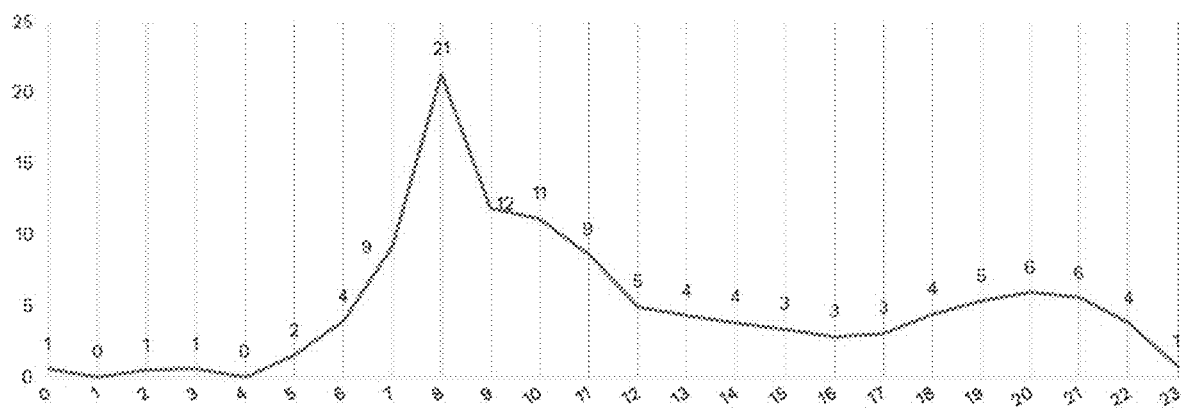
FIG. 3B is a plot illustrating high risk postures over time for a worker.

FIG. 1 illustrates a typical environment in which the system and method monitoring safety and productivity is deployed, FIG. 2A is a schematic for a sensor implementation for use in the method, FIGS. 2B-2D show one example of a sensor housing for the sensor of FIG. 2A, and FIGS. 3A and 3B are flowcharts illustrating such methods.

As shown in FIG. 1, workers, or other users of the systems and methods described herein, may be deployed to various locations within a warehouse 100 and may be required to perform a variety of repetitive material handling tasks at each location. For example, a first worker 110 may lift an object 120 from the floor to a shelf 130 in a first sector 135 within a warehouse 100, while a second worker 140 may lift a separate object 150 off of a shelf 160, rotate, and transfer it to a table 170 in a second sector 180 of the warehouse 100. Additional activities may include a worker 172 unloading a truck 174 which may include walking up and down a ramp 176, jumping, or operating machinery, among other activities. It will be understood throughout this disclosure that references to a worker are references to users wearing the wearable devices 190 discussed herein.

Each of the workers 110, 140, 172 would typically be wearing at least one sensor device, and in some embodiments, two sensor devices, 190a, b for recording movement. Typically, where two sensors are provided, the sensors used may be a wrist sensor device 190a, ideally located on the wrist or forearm of the dominant hand, and a back sensor device 190b, ideally located approximately at the height of the L1 and L2 vertebrae, but other sensor device types may be implemented as well. The wrist sensor may incorporated into a wrist device, such as a bracelet or a wristwatch, and the back device may be incorporated into a chest strap, weight belt or back brace, for example. Where only one sensor device 190 is provided, it is typically applied to a worker 110, 140, 172 on or near the worker's hip. However, the device 190 may be applied elsewhere and the necessary dimensions and measurements may be extrapolated from data recorded from the sensor device 190. The sensor device 190 may take a variety of forms, and is referred to herein as any of a sensor, a device, or a sensor device.

Accordingly, a single sensor device 190, referred to herein as a wearable device, may be used to record movement. Such a sensor may be mounted on a user's belt and may be used to predict or estimate motion of the user's back and spine based on movements of the user's hip. A system implementing such a wearable device may be trained using a machine learning predictive model trained by collecting data from sensors attached to a user's spine and comparing that data to data collected at the user's hip. After training such a predictive model, the single hip mounted wearable device 190 may be used to evaluate movement of a worker's spine.

Accordingly, in embodiments using a single wearable device 190, the wearable device is mounted at a workers hip, and the measurements calculated include measurements of a user's back inferred from movement of the user's hip detected by the wearable device. Such movement of the user's hip may be detected by the accelerometer 210, gyroscope 220, and altimeter 240, discussed above.

Figure 4A:
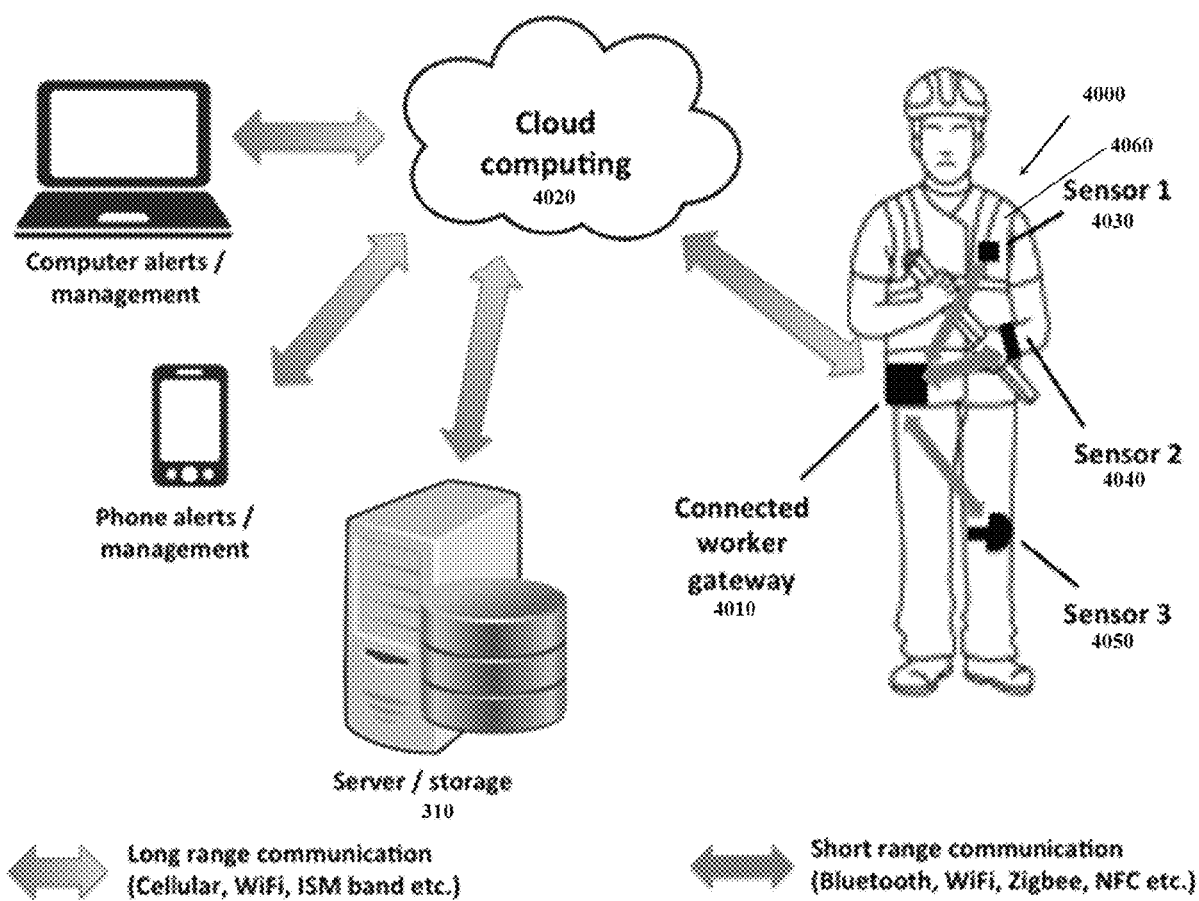
FIGS. 4A-C show systems in which the sensor and sensor packaging may be implemented.
Figure 4B:
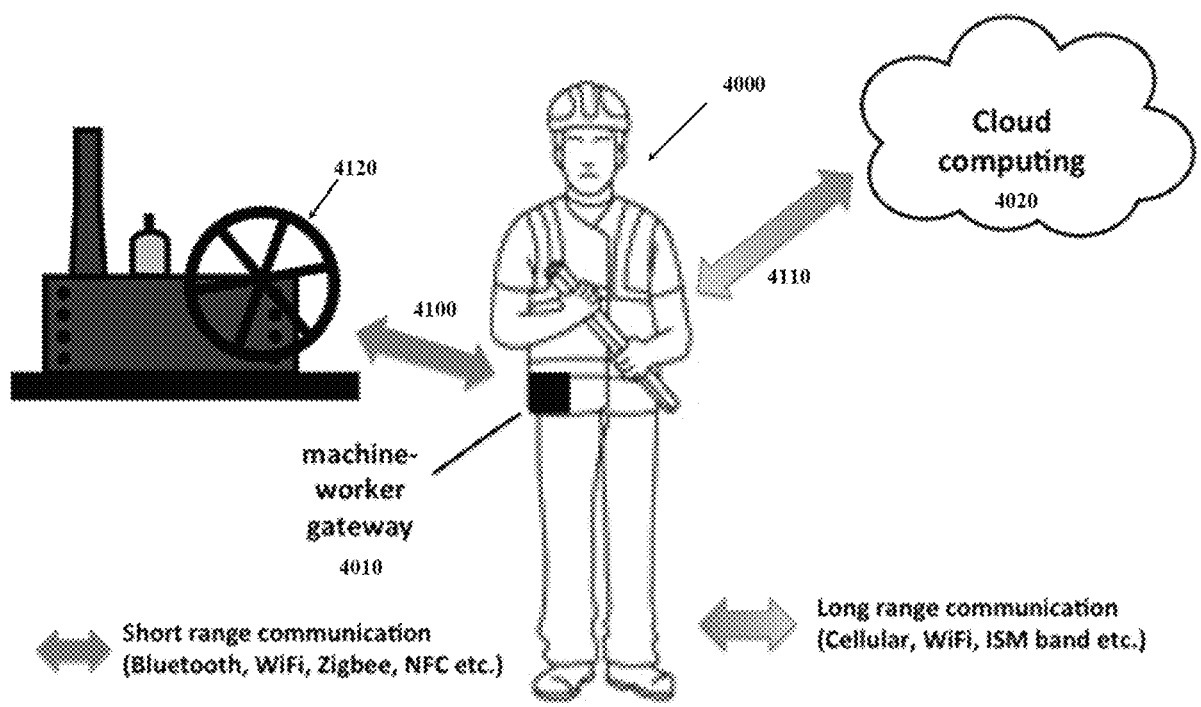

In some embodiments, a single primary wearable device 190 may be used and it may communicate with various sensors or transmitters on different parts of the user's body, as shown in FIG. 4A, in an environment in which the user is working, as shown in FIG. 4B, or on equipment the user is using. For example, a user may have a primary wearable device 190 that interacts with safety equipment worn by a user or with a humidity, temperature, or gas sensor located in a factory.

A server 310 may further be included in the warehouse 100 for receiving data from the wrist sensor 190*a* and the back sensor 190*b*, or the single wearable device 190, depending on the implementation, and storing records of activity performed by workers 110, 140, 172. In some embodiments, signals generated and transmitted by the wearable device 190 are received and processed by the server 310. In some embodiments, results of the methods discussed below are generated and retained by the wearable devices 190 and are used to provide immediate feedback to workers 110, 140, 172. In some embodiments, the results are transmitted to additional terminal devices 195 to be accessed by a third party, such as a manager, or by the workers themselves 110, 140, 172. While the warehouse 100 shown includes a physical server 310, it will be understood that the server may be a cloud server or may be coupled to a cloud server to maintain a platform implementing the method described.

In some embodiments, the results may be organized in a log for retention by the system. Such a log, discussed in more detail below, may be used by a manager to reschedule workers to tasks more suited to them. It may also be used by employees or managers to reorganize their time based on when they are most fatigued. Further, the log may be used by insurance companies to modify insurance rates and premiums based on employee risk profiles, either for individual employees or for a company taken as a group, as discussed in more detail below.

As shown in FIG. 2A, each wearable device 190 may include a sensor array 200 including a 3-axis accelerometer 210, a 3-axis gyroscope 220, a 3-axis magnetometer 230, a temperature sensor 240, and an altitude sensor 250, such as a barometric pressure sensor. Each sensor device 190 may further include a communication module 260 which may include multiple communication interfaces. For example, each sensor device 190 may have a short range communication interface 270 for enabling communications between a first sensor device 190*a* and a second sensor device 190*b* worn by a single user. The short range communication interface 270 may further be used to receive signals from additional sensors or devices on the user's body, such as safety equipment, or from sensors or other transmitters in the user's immediate environment. The wearable device 190 may further contain a longer range communication interface 280 for connecting, for example, to a Wi-Fi or cellular network. Each wearable device 190 may further include a computation module 285, including a processor 290 and a memory 300.

Accordingly, each of the sensor devices 190*a*, *b*, may communicate with each other (in embodiments where users wear multiple sensor devices), or other local devices or sensors, using the short range communication interface 270 and with the server 310 or a cloud network using the longer range communication interface 280. Signals generated by the sensor devices 190 may be processed at the individual devices, may be combined with other data acquired through the short range communication interface 270, or may be transmitted to the server 310 or another centralized platform for analysis.

The wearable device 190 may further incorporate a feedback module 320 for providing feedback to the user. For example, the feedback module 320 may include a motor for generating vibration and providing haptic feedback, audible feedback in response to the output of the method, and/or a display for visual feedback that can show immediate as well as cumulative risk exposure. Further, different levels or patterns of vibration in the context of haptic feedback may be used to indicate different alerts to the user of the device. The wearable devices 190 may further incorporate user input means by which users can control the wearable device 190. For example, the device may include modules for detecting and interpreting voice or gesture based commands.

The wearable device 190 may have an additional module for determining location by, for example, incorporating a GPS unit or other geolocation components and processes. Alternatively, or in addition to geolocation components, the wearable device 190 may include a module for triangulating the location of workers based on proximity to known landmarks, such as beacons.

The sensor devices may further include batteries for providing power to the various modules therein. The sensor devices may further incorporate LEDs, displays, or other methods for delivering feedback to the workers 110, 140, 172 wearing the sensors. For example, the device may utilize a display to display the risk metrics, or a goal, rank or other relevant information like battery and signal status. The display may be touch sensitive in order to provide a user interface by way of the display. Other information displayed can be error or warning messages when a worker is detected to not be wearing the device correctly, or in a variety of other scenarios discussed below in more detail. The device can also show information like number of steps taken by a worker, calories burned, active hours in the shift, current time and the time to next break etc. This information can be shown when a worker requests it, at regular intervals, or automatically when one of the methods described below are used to identify a relevant or hazardous situation.

In some embodiments, the user interface is replaced by, or supplemented by, a separate portable device or an application for use on a smartphone. In such a case, when an alert is triggered, such alert may be transmitted to a user on his smartphone.

FIGS. 2B-D show a sensor packaging 2000 containing a clip 2010 for fixing the sensor device packaging 2000 to a user. The sensor device 190, as discussed above, must be attached to the body of a user, typically in a predetermined location or in one of several potential predetermined locations. Once attached, the relative motion between the user's body or clothing and the sensor device 190, which would be noise in a signal generated by the sensor, should be minimal. Accordingly, a robust fixation mechanism, combined with appropriate calibration methods, described below in more detail, are useful to reduce signal noise and increase the accuracy of the various methods described.

FIG. 2B shows a sensor packaging 2000 having a clip mechanism 2010 in an open position for fixing the sensor to a user's clothing. The clip 2010 includes a lever 2020 which, when rotated, converts its rotational motion into horizontal motion of a clip, such as wire clip 2025, using a cam mechanism 2030. The cam mechanism 2030 uses a cam surface 2040 and a pin 2050 interacting with a track 2060 in order to implement horizontal motion in the wire clip 2025. When the lever 2020 is fully lifted, as shown in FIG. 2B, the wire clip 2025 is separated from a back surface 2070 of the sensor packaging 2000, providing a space for the user to place the device over their belt or trouser rim. As shown in FIGS. 2C-D, once the sensor packaging 2000 is in position, the lever 2020 is rotated towards the sensor packaging 2000, which draws the wire clip 2025 towards the back surface 2070 and then compresses the user's belt or trousers by applying a normal force to the clothing, minimizing the motion between the sensor packaging 2000 and a user's clothing.

The normal force applied by the clip design can be varied by modifying the parameters of the wire clip, which acts like a spring. The length, design and material can all be modified to obtain a required normal force. In addition, a high friction material can be placed between the wire clip and back part of the enclosure to increase the friction force between the device and the clothing. For example a rubber coating can be placed on the wire clip, or a rubber overmold may be placed on the back surface 2070 of the sensor packaging 2000. The wire clip can also be modified to increase its range of motion by adding torsion springs or other similar design methods.

The clip 2010 described may further comprise a switch activated by the closure of the clip. For example, the clip 2010 may include a magnet incorporated into the lever 2020, such that a magnetic field sensor, such as a reed switch, may be used to determine when the sensor packaging 2000 has been applied to a user's person. Accordingly, when the clip 2010 is closed on a user's belt, the switch may indicate that the sensor 190 has been positioned, and the device may initiate a calibration process, as described in more detail below. Similarly, a capacitive surface incorporated into the clip 2010 may be used to confirm that the clip has been closed. Alternatively, a physical switch or button may be included to indicate that the sensor packaging 2000 has been properly positioned, and that the sensor 190 may now begin to capture data, or a proximity sensor or a light sensor may be incorporated to detect when the sensor packaging 2000 has been placed on a user's body.

While the components of the two sensor devices 190*a, b* are described identically in embodiments in which two sensor devices are utilized, in some such embodiments, the sensors comprise different components. For example, the wrist sensor 190*a* may not include a longer range communication device 280 or a computation module 280 and may instead immediately transmit signal data to the back sensor 190*b*. The back sensor may then process the data and transmit results to the server 310.

Other implementations are possible as well. For example, all signals may be immediately transmitted from the wearable device 190, to the server 310 which in turn implements the methods described. For the purposes of outlining the methods performed, the methods will be described with respect to such a platform where processing is handled centrally at a server 310. However, it will be understood that the calculations and methods described may be performed at any one of the wearable devices 190 described, or across a combination of the wearable devices discussed. Further, while the method described in reference to FIG. 3A discusses a system using signals separately acquired from two sensor devices 190*a, b*, all required measurements may instead be acquired from a single wearable device 190. In such an embodiment, a single signal may be analyzed. Further, while some methods described detect lifting activities, other physical activities may be detected as well, as discussed in more detail below.

Accordingly, while workers perform material handling tasks and other physical activities, including lifting objects 120, the server receives both a signal from the wrist sensor 190*a* indicative of the movement of that sensor over time (400) and a signal from the back sensor 190*b* indicative of the movement of that sensor over time (410). This may be received in the form of a data stream or a transient signal, or it may be received in the form of chunks of data received consecutively.

The server then evaluates (420) both signals to determine if any portion of the signal represents the initiation of a lifting activity. If a lifting activity is identified in the data, the server then further evaluates (430) both signals to identify an end point of the lifting activity. In some embodiments, this detection of an initiation of a lifting activity and an end point of the lifting activity is by way of a rules based approach directly using variables obtained from the sensor data, or based on variables detectable after only minimal signal processing. This rules based approach may include, for example, measuring the back angle with respect to the gravity plane and determining when it passes a threshold. This type of threshold may be static or variable, depending on other elements of the lift. Arm elevation angles may further be used to detect lifts above the shoulder, for example.

In some embodiments, the signals are used to identify only an initiation of a lifting activity, but not an end point of the lifting activity. In such an embodiment, a lifting activity may be assigned a specified time limit, such that the lifting activity is assumed to have concluded after a fixed amount of time has passed.

In embodiments with only minimal signal processing prior to identifying the initiation of a lift may comprise only filtering of data to reduce noise and cancel any drift. Typically, filtering is applied, such as a band pass filter, to ensure that more resource intensive processing is applied only once a lifting activity is detected within the more minimally processed data. For example, drift in height sensor data and gyroscope data may be filtered to reduce noise prior to identifying a lifting activity, and then the filtered data may be utilized to detect the initiation of a lifting task with a reduced number of false positives.

In some embodiments, the lifting activity will be single lifting motion. In others embodiments, the lifting activity may comprise the entirety of the moving of an object from a first location to a second location. For example, the lifting activity may comprise a first user 110 picking an object 120 up off the floor and placing it on a shelf 130. Similarly, the lifting activity may comprise a second user 140 picking up an object 150 off of a shelf, rotating, and placing the object on a table 170. Alternatively, the lifting activity may be a simple lifting action in preparation for a secondary action, such as walking with the package.

Once a beginning and end point of a lifting activity is identified, the portion of the signals from the wrist sensor and back sensor between the initiation and end point of the lifting activity are excerpted (440) from the signal to generate a first segment of data corresponding to lift data from the wrist sensor and a second segment of data corresponding to lift data from the back sensor.

In some embodiments, data from the point of time of the initiation of the lifting activity is taken and is processed immediately upon detecting the initiation of a lifting activity. In such a way, risk models depending only upon static posture at the time of lifting may be implemented immediately and may provide results before the completion of the lifting activity.

Optionally, the method may then evaluate (450) a portion of the signals from the time period immediately before lift and immediately following the lift. This may be used, for example, to eliminate false positives prior to incorporating such results into statistics being reported. For example, when a worker bends over to lift something outside the scope of his task, such as a worker bending down to lift a pen from the floor and place it in his pocket. In such an example, the initial back bending angle and lowering of the wrist, as measured by wrist height, would indicate a lifting event. However, since the wrist would then align with hip of the worker and the back of the worker would straighten, this would not be considered a lifting event. Accordingly, the portion of the signal immediately following the lift may then clarify that the lift detected would constitute a false positive for the purpose of statistics being gathered.

Once the portions of the signals corresponding to lifts are excerpted, the method processes (460) the excerpted portions of the signal to extract metrics required for risk models being evaluated. The processing of the excerpted portions of the signal typically incorporates methods designed to increase signal to noise ratio and otherwise improve the quality of the data. This may include methods such as low pass filtering, Kalman filters, Gaussian moving averages etc., all of which combine to reduce the noise in the signal and remove unwanted drift of signals, such as the barometric pressure signals, from the sensor data. From the signal processing, the method may compute several new variables such as back sagittal angle or wrist elevation angle, as discussed further below.

In some embodiments, some amount of signal processing occurs prior to step 420 so that a signature in the data corresponding to a lifting activity may be more consistently identified. Such a signature may be used to detect sequences associated with lifting tasks, such as box grabbing, carrying, and dropping. In other embodiments, the data is checked after the excerpts have been processed to confirm that a lifting activity has indeed occurred. For example, the data from the back sensor 190b may be monitored to determine when a worker's back has bent over a certain amount. This information may be coupled with data from the wrist sensor 190a to increase accuracy. While the method is described with respect to a lifting task, it will be understood that the task may be any number of physical tasks, such as a known sequence of motions for assembling a device or a specific task such as rebar assembly within the construction industry.

Where the risk model being evaluated is the NIOSH lifting equation risk model, the method extracts (470) from the data the following values:

H—a horizontal location of the object being lifted relative to the body. This may be determined, for example, by evaluating the horizontal difference in location between the wrist sensor 190a and the back sensor 190b and accounting for known offsets based on the angle of the back sensor 190b, and the known thickness of the trunk of the worker being evaluated, as well as the offset from the workers wrist to his hands.

V—a vertical height of the object being lifted relative to the floor. This may be determined, for example, using a height sensor in the wrist sensor 190a, such as the barometric pressure sensor 250 and further utilizing some of the signal processing techniques discussed below.

D—distance the object is moved vertically. This may be determined by calculating the difference in height at the time of initiation of the lift and the conclusion of the lift. In cases where the lifting process being evaluated includes both picking up and putting down the object, this may be the difference between the highest and lowest heights measured during the process.

A—asymmetry angle is a measure of how much the workers back is twisted during the process. Where a worker 140 picks up a package 150 in a first location 160 and places it down in a second location 170, the amount of rotation of the workers back is measured and evaluated. This may be evaluated by extracting the data from the gyroscopic sensors in the back sensor 190b and applying an offset based on the workers trunk thickness.

F—frequency of lifts performed, as computed from lift detection algorithms.

In some embodiments, duration of lifting tasks may be implemented, as computed by the time lifting activities have occurred and have been detected by lifting algorithms.

In some embodiments, an additional variable, C, may be incorporated and evaluated to assess the quality of the grip of a worker on a package.

The processing associated with these variables, as well as those below may include computing a gravity vector from quaternion data, which is obtained from the fusion of gyroscope and accelerometer sensor data. In such embodiments, acceleration in both horizontal plane and vertical direction may then be computed using the gravity vector. Threshold based outliers may then be removed from the data. Components of the back and wrist elevation angles are then computed using components of the gravity vectors.

Several required variables may be detected or confirmed by way of machine learning algorithms. Similarly, the accuracy of lift detection may be improved by way of machine learning algorithms. Such algorithms may further be utilized to confirm the identification of the activity detected, both in terms of improving the detection of true positives and eliminating false positives. More broadly, such algorithms may improve the precision and recall of lift detection and variable evaluation. Statistical features monitored by such machine learning algorithms may include:

Lagged cross-correlations between variables;
Dominant frequency components of the signal;
Movement intensity statistics;
Movement energy statistics;
Signal magnitude area; and
Window duration.

All of these statistics may be monitored over windows of data which may be calculated based on elements of the signal, such as those detected above in steps 420 and 430.

As discussed above, some variables may be detected directly from the sensor data while others require further processing. Since several variables are inferred, rather than detected directly, the method may utilize confidence intervals in the estimates and may report results, as discussed below, in the form of either conservative or aggressive approaches, to calculate risk metrics. Such approaches may be selected by a user operating a platform implementing the methods.

The height of sensors is typically extracted from a barometer, or other types of altimeters. Data from these sensors tend to drift. Accordingly, the drift may be corrected by coupling the sensor data with acceleration data in the gravity direction in a Kalman filter. This may also be done by way of a low pass filter for certain types of altimeters. Further, the height detector may be calibrated by setting the height to a known value upon the initiation of a lift. For example, the height of a back sensor may be set to a fixed value at the beginning of each lift, regardless of whether the worker is, for example, standing on a stool.

In some embodiments, some initial signal processing is applied to the signals upon receipt so that the detection of the beginning of a lifting activity may be made with more accuracy. The initial signal processing may then be followed by more advanced signal processing and machine learning algorithms for extracting remaining variables from the data and for confirming that a lift actually occurred during the time period excerpted from the signal.

Besides travel distance for a specified value between the beginning and conclusion of a lifting activity, each variable may be independently evaluated with respect to the beginning of a lifting activity detected and at a conclusion of a lifting activity detected. For example, where a worker 140 moves a package 150 from a shelf 160 to a table 170, if the worker faces the shelf while doing so and twists his back 90 degrees to deposit the package 150 on the table 170, his angle will be 0 for the beginning of the lifting activity and 90 for the end of the lifting activity.

Other ergonomic risk models may be implemented as well, and may require extracting different values from the data. For example, if implementing the risk model developed by Marras et al using his Lumbar Motion Monitor, the data extracted from the signals may be:

Average twisting velocity of the torso during the lift activity, computed in a way similar to the calculation of the asymmetry angle discussed above, except using angular velocity.

Maximum moment on the lower back, which is computed by multiplying the maximum horizontal distance between the load and the worker's trunk and the weight of the object lifted.

Maximum sagittal flexion of the torso, which is determined by extracting the offset bending angle of the lower back relative to a vertical axis (usually gravity).

Maximum lateral velocity of the torso, which may be determined from the accelerometer gyroscope in the back sensor.

Frequency of lifts specified in lifts per minute, which can be obtained from the frequency of lift detection.

In some embodiments, the risk models specified may be used to calculate a maximum recommended lifting weight based on a workers lifting technique. This is done by using the variables extracted from the signals in a risk model. For example, the NIOSH risk model may be used to calculate a recommended weight limit. Further, the model may be used to calculate a lifting index identifying a risk associated with any particular lifting action or task. Further, while the model is discussed in terms of lifts, such a model or a similar model may be used to evaluate other activities as well in order to determine a risk level for such activities. The model used may then provide numerical results, or those results may be classified in terms of low, medium, and high risk lifts. Similarly, underlying values for variables may be implemented directly in the models, or they may be mapped on to low, medium, or high values.

Using the NIOSH risk model as an example, a recommended weight limit for a single lift may be calculated by simply determining each of the values discussed above, determining an appropriate multiplier used in the model (typically determined from a table associated with the model, or by calculating an appropriate ratio) and multiplying the relevant multipliers. Accordingly, the recommended weight limit may be determined from the equation $RWL=LC*HM*VM*DM*AM*FM$ where LC is a constant multiplier for the formula, typically 51 lbs., and HM, VM, DM, AM, and FM are the multipliers associated with the calculated values of H, V, D, A, and F respectively. In some embodiments, an additional multiplier may be used to incorporate the duration of lifting tasks. While the NIOSH risk model is described, other risk models may be implemented as well. Further, by dividing an actual weight lifted by the recommended weight limit generated by the NIOSH model, a lifting index may be generated providing an evaluation of the risk associated with a specified lifting activity.

Further, data from individual workers may be correlated with personal information for that worker. For example, a specific worker's data may be correlated with that workers height, history of back injuries or other medical issues, or other physical or personal characteristics that may affect performance. Further, measures of physical characteristics may be estimated, such as arm length for workers, which can in turn be used to improve both the ability to infer variable values from signal data and the ability to use the variable values detected.

While NIOSH and Marras models are described, other risk models may be utilized as well, such as Liberty Mutual® tables, RUBA, RULA, and others. For example, the signals from the sensor 190 may be used to estimate the compression at a specified vertebrae of the spine using a biomechanical model. That compression may then be compared to a maximum limit, such as the 770 lbs. prescribed by OSHA, in order to classify a lift as potentially high risk.

In this way, the selected risk model may be used to determine a maximum recommended weight for any given lift (480). Where the risk model used supports a determination for a single point in time, the risk model may be implemented immediately following the detection of an initiation of a lifting activity at step 420. In such an embodiment, the information from the moment of time detected is immediately extracted and processed.

Optionally, the method may extract (490) from the data an approximation of the actual weight of a package lifted. Such an approximation may be calculated by evaluating the angular velocity or acceleration of the wrist sensor 190a. In some embodiments, this may be compared (500) to the same metric for a known weight such that the weight of an object may be inferred by comparing the angular velocity of a specified lift by a worker to an angular velocity associated with a lift for a known weight by the same worker. The accuracy of this measurement may be further improved by evaluating data related to the angle of the back sensor 190b and similarly mapping it to known angles for known weights by the same worker.

Similarly, metrics correlated with energy applied during a lift may be implemented. Such metrics may draw signals from both the back and wrist sensors and may be used to evaluate the weight of an object lifted.

The various signals evaluated upon identifying a lifting motion may then be used to detect acceleration in the vertical direction in the world frame of reference. Accordingly, when a worker begins a lifting process, the wrist based accelerometer may immediately detect a jerking motion as the height sensor begins to rise from its lowest position. The velocity of the rising motion may then be used as a proxy for effort applied in lifting, which in turn may be used as a proxy for determining the weight of an object lifted. Such an approach may determine both the weight of the object being lifted or, if the weight of the object is known, the fatigue of the worker lifting the object. Either approach will allow the system to determine an effective weight of the object from the perspective of the worker. Including the fatigue of the worker lifting the object in this way may further incorporate a fatigue component in evaluating risk to the worker.

In such an embodiment, the approximate weight or effective weight calculated is then compared (510) to the maximum recommended weight (determined at 480) based on the model.

If the weight lifted is greater than the maximum recommended weight, the sensor may provide feedback (520) to alert the worker to the weight limit. Such feedback may be, for example, haptic or audible feedback. In some embodiments, a combination of feedback methods may be implemented, and the feedback may then be displayed on a screen associated with the device or through an LED, and haptic feedback may be implemented to prompt the user to view the screen.

While the method is described in the context of a weight limit in the context of lifts, additional risk metrics are contemplated as well. Such metrics may be used to evaluate risk for any activity, including the lifting of packages. Accordingly, the risk metric generated provides a proxy for risk of an activity, or set of activities, performed by a worker, and the system and method may then compare that metric to a threshold to determine whether the activity as executed is high risk.

While the method evaluates individual activities, the server will continue to receive data from the sensor devices 190a, b. Accordingly, the server may then store (530) a record of the first lift in a memory associated with the server and return to step 400 and continue monitoring the sensor data to determine if the worker is performing additional lifting activities. The server typically continues to monitor the data for additional lifting motions over the course of an evaluation period. In some embodiments, once multiple lifts have occurred, the method calculates (540) a frequency associated with the lifting motions identified and incorporates (550) that value into the risk models in order to monitor and evaluate risks associated with repetitive lifts. Such frequency data may be used in the NIOSH model described above, for example, to reduce the maximum recommended weight for a repeated lifting activity based on repetitive stresses and associated risks.

After the conclusion (560) of an evaluation period during which lifting motions are evaluated, the risk models may be used to evaluate (570) aggregate risk over the time period. In some embodiments a worker's shift may be divided into blocks of time, such as half hour blocks, for use as evaluation periods. In some embodiments, the evaluation period is instead the entirety of the worker's shift.

Figure 3C:
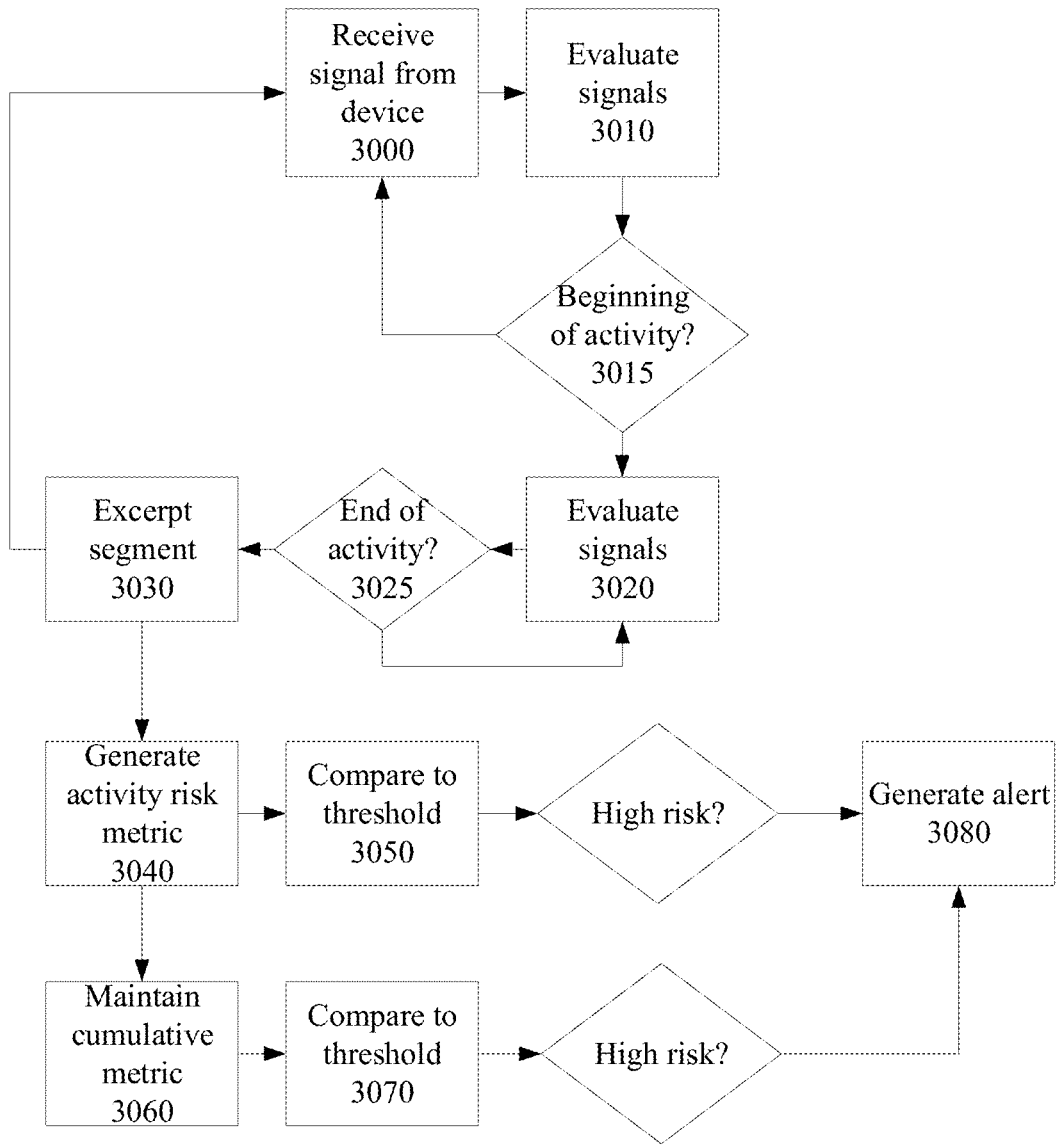
FIG. 3C is a flowchart illustrating a method for monitoring safety.

FIG. 3B is a plot illustrating high risk postures over time for a worker, and FIG. 3C is a flowchart illustrating an alternative method for monitoring safety. While the basic method discussed may provide an alert, such as a vibration or device display indicating a high risk physical activity or movement any time such a movement was performed, such an approach may result in a large number of alerts to a worker. Such a large number of alerts may be ignored, or may irritate the worker. Accordingly, a separate metric, described herein and mentioned briefly above, may be used to evaluate accumulated risk over a period of time, and that metric may be used to determine whether a worker should be alerted for each individual high risk physical activity. This may take the form of a running gauge over a time window.

Generally, in such an embodiment, if frequency and/or magnitude of accumulated high risk motions is above a threshold, the device would then alert a worker for every high risk motion until the risk is reduced by either reduce the high risk motion, such as by changing posture, or by using assist equipment or resting, or by switching to a lower risk job function.

It is well known that a high frequency of high risk postures can lead to an increase in musculoskeletal injuries. Frequency would indicate a certain number of postures or high-risk postures in a period of time. For example, FIG. 3B shows a plot of the number of high-risk postures a worker performs over the course of a day. Clearly from 7-9 am there is an increase in high-risk postures due to some work related activity.

Accordingly, in some embodiments, the method may evaluate aggregate or accumulated risk, in the form of a cumulative risk metric, and risk associated with individual activities in combination. Such a combination allows for the leveraging of risk based insights. As shown in the flowchart, an entity implementing the method, such as a server 310 or a wearable device 190, may receive a signal generated from dynamic activity of the wearable device over time (3000). The method may then evaluate the signal (3010) and determine if a first physical activity was initiated (3015) by identifying an initiation time for the physical activity performed by the worker wearing the device 190. The method then evaluates the signals further and calculates measurements of the worker wearing the device 190 for the time period during the first physical activity from the first signal segment for a time period following the initiation time (3020).

The window over which the first physical activity is evaluated is typically closed at the conclusion of the activity. At that point, the signal segment corresponding to the first physical activity may be excerpted (3030) and used for further evaluation or storage. For example, it may be stored in a log of activity, as discussed in more detail below.

The determination of a conclusion time (3025) for a particular physical activity may be based on recognizing such a conclusion in the signal. As discussed above with respect to FIG. 3A, the detection of an end point of a physical activity may be based on a rules based approach, or it may be based on a specified time limit. For example, if the physical activity is a lift, the method may assume that the lift will take five seconds.

Accordingly, the calculation of the measurements of the worker wearing the device is then used to generate a risk metric (3040) associated with the first physical activity. As discussed above, the activity risk metric is derived from a risk model based on the measurements of the wearer during the corresponding physical activity, and is indicative of a risk level for the corresponding physical activity.

The risk metric derived (at 3040) may then be compared to an activity risk threshold (3050) to determine if the first physical activity was a high risk activity.

While the risk metric is derived and evaluated, the method continues to evaluate additional physical activities identified in the signal. This is by repeating the identification of an initiation time by evaluating the signal (at 3010) and calculating measurements of the worker wearing the device 190 for a time period following the initiation time (at 3020).

The method then repeats the generation of an activity risk metric (at 3040) for each identified physical activity from the risk model based on measurements of the wearer during each physical activity.

In addition to the activity risk metric generated for each identified physical activity (at 3040), the method also generates, or maintains, a cumulative risk metric (3060) indicative of a risk level from multiple physical activities over time.

The method then determines if the cumulative risk metric (generated at 3060) is above a cumulative risk threshold (3070) at any given time. When a cumulative risk metric is above the cumulative risk threshold, a worker may be considered to be at high risk for injury if they perform additional high risk physical activities. Accordingly, if a user performs a physical activity, and the activity risk metric generated from that physical activity (at 3040) is greater than the activity risk threshold, such that the individual physical activity is considered to be a high risk physical activity, the method may then determine if the cumulative risk metric (at 3060) is above the cumulative risk threshold (3070). The method then generates an alert (3080) to the worker, or to a supervisor, only if the cumulative risk metric (at 3060) is greater than the cumulative risk threshold (at 3070) and the activity is considered to be high risk.

The cumulative risk metric may be for a sliding window of time immediately prior to the calculation of the activity risk metric (at 3040) for a particular physical activity. Accordingly, prior to generating the alert (at 3080), which may be, for example, haptic feedback, the method may determine if the user has been performing high risk physical activities over the most recent window. Such a window may be, for example, a half hour, or it may be longer, such as daily or weekly. Alternatively, the window of time may vary in length depending on the situation.

The cumulative risk metric may be, for example, a risk frequency metric. Accordingly, the metric may be a measure of the frequency with which the activity risk metric was above the activity risk threshold during the sliding window of time for the cumulative risk metric. The frequency threshold may be, for example, a specified frequency goal or an average number of high-risk postures over a full day. Accordingly, while the flowchart in FIG. 3C shows the cumulative metric being maintained (at 3060) based on the generated risk metric (at 3040), it may instead draw from the comparison (at 3050) to consider the frequency of the activity risk metric demonstrating a high risk. Similarly, it may draw directly from the excerpted segment (at 3030) or the signal data (at 3020) to determine a cumulative metric based on variables different from the activity risk metric.

Alternatively, the cumulative risk metric may be a measure of rest periods between instances of the activity risk metric being above the activity risk threshold. This may allow the cumulative risk metric to consider cumulative rest time. Alternatively, the cumulative risk metric may be a measure of the overall number of physical activities performed during the sliding window of time, such that the system may determine whether a worker is likely to be fatigued. Being fatigued from a large number of physical activities may result in a worker being more susceptible to the risk associated with high risk individual physical activities.

In some embodiments, the cumulative risk threshold used may change over the course of the day or across several days. Accordingly, the threshold may be lowered, and a worker may be more likely to receive an alert, during a time of day when the worker is fatigued.

In some embodiments, the cumulative risk metric may be based on kinematic variables including at least one of back bending angle and cumulative trunk loading. For example, the cumulative risk metric may be based on a time integration of the kinematic variables over time. Accordingly, in such an embodiment, the metric is based on an integration of the back bending angle over time and an integration of the trunk loading window over time. The cumulative risk metric may be based on variables different than those on which the activity risk metric is based, or it may be based on the same set of variables. Accordingly, the activity risk metric may be based on a first physical model while the cumulative risk metric may be based on a different physical model.

In this way, a worker can be alerted to high risk activities during a time when they are above the threshold. The device may alert the user, such as by haptic feedback, initially when the cumulative risk metric crosses the cumulative risk threshold. This would notify the worker when their unit has entered vibration mode. If the cumulative risk metric returns below the cumulative risk threshold, the device 190 would stop alerting the user for every high risk physical activity.

As a result, workers would get more buzzes at the times of day when their risky activity was at its highest (regardless of whether or not it is at start of shift or end of shift), and would ideally get fewer buzzes in situations like bathroom breaks, lunch times, etc. It would also give the safest workers the opportunity to not get buzzes at all during a given day even if they still do 5-10 high risk postures (HRP) here or there.

In some embodiments, additional cumulative risk metrics may be maintained by the method or system described. Accordingly, a worker may be monitored for cumulative risk over the window discussed above, as well as a complete day and/or week. Other cumulative variables may include cumulative trunk loading, position and timing variables, and integrated kinematic variables, such as daily integrated back sagittal angle or velocity.

In some embodiments, the cumulative risk metric may be used to trigger a modification of a design of a job assigned to the wearer. For example, if the cumulative risk metric is above the cumulative risk threshold for a specified amount of time, the design of the job for a specific worker may be modified to require the wearer to utilize assist equipment.

As discussed above, in addition to lifts, a variety of other physical activities and events are detectable. These other physical activities or events may include actual risk indications, as well as behaviors indicative of potential risk. For example, jerks, or sudden motion put extra strain on a worker's body, and such jerks may be identified by identifying spikes in the acceleration data. The amplitude of the spikes along with their distribution over time can be used to determine the intensity of and frequency of a jerk. If such jerks are overly frequent, or overly aggressive, a safety manager may be alerted to the activity.

Similarly, jumps can be detected and impact on the health of knees can be inferred. For example, a distribution worker might jump off of a truck with or without package in hands. The impact of jump on the knees can be detected by looking at spikes in the acceleration in the vertical direction and correlated with sudden changes in detected height. The magnitude of the acceleration and height when the jump occurs can give an indication of the intensity of the impact. This can be reported, and feedback provided to reduce the number of jumps that occur, or in order to reduce the intensity of the jumps. These jumps can often lead to impact and cumulative injuries on knees, ankles and hips.

In one embodiment the wearable device 190 could measure running within a facility where running is not recommended, or where surfaces could be conducive to slipping.

In another embodiment, the wearable device 190 could be used to measure when someone is climbing up a ladder, and the amount of time spent on each part of the ladder, or if a user is using an elevator, by monitoring a change in the user's elevation. The rate of change of height can help determine the action being performed.

In another embodiment, slips which do not lead to falls can also be detected, and considered as near misses. In addition, these episodes can also be used to log information about incidents, such as the time, and to which worker they happened to.

In another embodiment, the wearable device 190 can be used to evaluate the driving of vehicles such as trucks and forklifts, or the use of other industrial equipment. Based on the acceleration and deceleration profiles, worker driving can be evaluated and scored. The number of hard braking actions or extreme acceleration can be tracked. Speed of the vehicle can be estimated and if it surpasses a certain threshold, then action can be taken. In addition, if the vehicle is involved in an accident or an impact, it can also be detected and timestamped and data of the impact can be preserved for future investigation.

Further, an activity log for a user over time can help determine if they are exposed to gradual risks. The platform described may detect a number and frequency of repetitions doing a specific task, a number of steps taken, and an amount of motion, vigor of motion, time spent seated or standing or moving. These various factors can help determine the amount of fatigue and necessary resting period to help recover. As discussed below, the system may further incorporate environmental factors, such as localized humidity, in order to refine a model for the amount of fatigue a user might be experiencing. Such additional detail may be from environmental sensors, or from additional sensors incorporated into the wearable device 190 to measure, for example dehydration. Alternatively additional sensors may be worn elsewhere on the body, as discussed in relation to FIG. 4A below. The activity log may also be used to evaluate user productivity or evaluate other results of physical activities, such as accidents, as discussed in more detail below.

For example, an activity log may be used to determine a worker's schedule and shift scheduled activities to create optimal rest/work intervals. The system may use worker data to determine the effectiveness of their recovery periods, and thereby suggest schedule changes. The system may integrate with necessary systems at the facility to ensure that recovery schedules do not compromise business demands. Further, the system may incorporate worker preferences and company preferences in order to improve work/life balance.

Figure 3D:
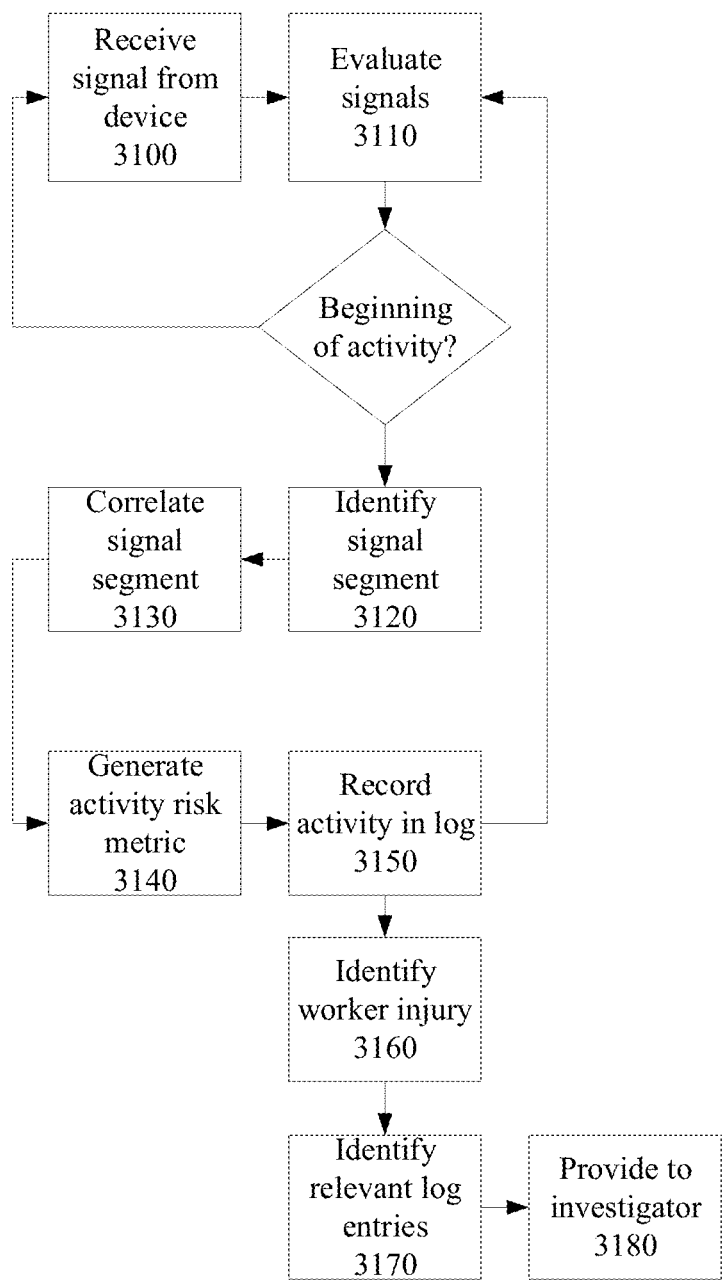
FIG. 3D is a flowchart illustrating a method of generating an activity log.

FIG. 3D provides one example of a method for developing and leveraging a log of activity in the context of the methods and systems discussed above. Accordingly, an entity implementing the method, such as a server 310 or a wearable device 190, may receive a signal generated from dynamic activity of the wearable device over time (3100). The signal is indicative of physical characteristics of the wearable device over time. The method may then evaluate the signal (3110) and identify (3120) a first signal segment corresponding to one of several expected categories of physical activities. Such a category of physical activity may be, for example, a lifting activity, a jumping activity, a climbing activity, or others. The first signal segment is then correlated (3130) with the corresponding category of physical activity, such that the signal segment can be evaluated in the context of the particular physical activity it corresponds to.

Once the first signal segment is known to correspond to a particular category of physical activity, an activity risk metric is generated (3140) for the first signal segment. This may be by using any of the methods discussed above for generating an activity risk metric. The method then records the signal segment, along with the category of physical activity and the value of the activity risk metric in a log (3150) associated with the particular worker associated with the wearable device 190.

The method then repeats the evaluation process to identify a plurality of signal segments, each corresponding to at least one of the several expected categories of physical activity (at 3120). Each signal segment is then correlated (at 3130) with the corresponding category of physical activity, and is then used to generate a corresponding activity risk metric.

Each individual signal segment is then recorded in the log (at 3150) in order to generate a log of physical activity performed by the worker associated with the wearable device 190, such that the log defines the category of physical activity, the activity risk metric, and the time for each signal segment. The log may record additional data, such as the location of the physical activity. In some embodiments, the log may include a complete record of raw data recorded at the wearable device 190. In addition to raw data, the log may further include any calculated angles or metrics evaluated by the wearable device, as well as any kinematic variables, temperature, air pressure, and height measurements and changes at the time of the associated signal segment.

In addition to data received from the wearable device 190, the log may further define environmental data, such as temperature, air pressure, air quality, and the like retrieved from other sensors or devices in the environment. For example, the location of nearby forklifts may be incorporated, as well as sensor readouts from nearby sensor beacons.

The correlation of the first signal segment, as well as each subsequent correlation, with the corresponding category of physical activity (at 3130) may be performed in several ways. In some embodiments, the wearable device 190 monitors a location of the device, using a geolocation module. Accordingly, the entity implementing the method may receive such an indication of the location of the device, and may then select the several expected categories of physical activities based on physical activities expected at the location of the wearable device at the time of the associated signal segment. For example, the wearable device 190 may indicate that the worker is in the warehouse adjacent a shelving unit. This may indicate that the worker is either lifting objects from the floor, or a cart, onto a shelf, or lowering objects from the shelf to the floor or cart.

In some embodiments, a cumulative risk score can be attributed to a geolocation along with a worker or job function. As such, individual locations in the warehouse may be identified as high risk and selected for reconfiguration by management.

Alternatively, in some embodiments, the signal segment may be directly compared to an expected signal segment corresponding to each of several potential categories of activity. The set of potential categories may be a complete set of categories available for analysis, or it may be a subset of potential categories selected based on context. For example, the subset may be based on a worker's location in a warehouse, as discussed above, or it may be based on a set of activities that the particular worker is scheduled to perform.

Alternatively, the correlation may be based on an expected activity by a worker based on a schedule, or it may be based on an action taken by the user to initiate a physical activity. For example, the user may scan a package prior to lifting it.

The log may then be used to investigate workplace injuries. A physical activity identified in the log may result in an injury to a worker. Alternatively, in some embodiments, one or more category of physical activities monitored in the method may be forms of worker injuries. In such an embodiment, the method may proceed by identifying, in the log, a physical activity corresponding to a worker injury (3160), identifying a set of log entries relevant to the worker injury (3170), such as the previous one or several physical activities, and providing such relevant log entry, including complete raw data recorded at the wearable device, to an investigating entity (3180). Accordingly, if an employer is investigating a workplace injury, they may be provided with a segment of the log corresponding to a time period immediately preceding the injury. Such data may be used to determine the root cause of the incident, and to determine or exempt a user from culpability.

Further, the platform monitors the worker's orientation at any given time. Accordingly, in the event of a falls or stumble, the device can determine the severity of the fall by measuring the acceleration and angular velocity. Using the orientation, the wearable device 190 can also determine if the worker has been in an improper orientation for an extended period of time, and can trigger an alert or an alarm to prompt appropriate action. Further, the platform could measure falls happening on the same level or falls happening on different levels. The combination of acceleration, direction of gravity on the device, and the change in height would allow the detection of a fall, and also the position of the worker on the ground.

In some embodiments, the wearable device 190 may detect individual motions, such that the device may detect unsafe postures, such as high-risk bends, twists, and reaches, as well as jumping off of vehicles or slips, trips, and falls. It can also detect safe postures, such as squats. Using algorithms that can distinguish different activities, the log can provide a mapping of all activities of a workers day (or other period of time) in order to map what percentage of the time is performed in safe postures, unsafe postures, driving a forklift or other vehicle, taking a break, walking, etc.

In some embodiments, the log may be used to characterize all activities of a worker into safe activities, such as a squat for lifting, pivoting instead of twisting, and the like, unsafe activities, such as high risk bends, twisting, jumping off of trucks, or reaching, and neutral activities, such as walking or standing.

Accordingly, while the log is discussed in terms of evaluating injuries, all activities performed by a worker in a day may be analyzed in order to generate a complete risk profile in the form of a risk score over time. Accordingly, a pattern may emerge that demonstrates a high likelihood of an injury occurring soon, so activities may be investigated before an injury or incident has occurred. This would help understand and predict the propensity to injury of the specific workforce.

As discussed in more detail elsewhere, the log may be used by actuarial processes to price risk of injury, or other metrics, into insurance policies. Accordingly, instead of blanket insurance premiums for a company, workers may be categorized based on their personal ergonomic risk profiles. Insurance policies could also be priced dynamically based on worker performance. Similarly, the volume of workers at the facility could impact the price of insurance.

The logs generated for multiple users could be mapped to a floor plan or map of the facility to see what activities occur at each location, and to optimize the design of the location for the activities that take place there. Risky areas can be mapped in order to help prioritize which areas of a facility should be redesigned. The log could further be used to evaluate the types of activities performed by people who rarely get injured.

Further, using the log generated, an action center may be provided for managers. The methods for the action center would involve processing the worker data, finding certain cues that would trigger an action, and display that action for managers or workers to view.

Managers and safety personnel can then review prescribed real-time invitations to action based on safety metrics for individual workers, and predictions of future injuries. For example, when a worker is engaged in a task and their rate of high-risk postures is unusually high, the system can alert the personnel team in order to make an informed decision. Alerts may relate to increased energy expenditures, higher than average wear time, risky biometrics, and other alerts. Such alerts can be sent to managers and/or wearers of the devices.

The method may then predict and prevent injuries based on historical injury data. In providing real-time decision information data, the method uses historical data to predict the likelihood of future injuries using the data from the device 190. When injuries are predicted, or the probability of injury increases, the users or managers will be alerted and courses of action may be determined.

Groups of workers with similar risk profiles and movement patterns can be addressed and trained by managers as a group. Such groups may be identified in the form of common movement patterns across several workers. For example, workers with more bends than twists will be grouped together to discuss techniques and strategies to mitigate those risky behaviors. Groups can be altered based on flexible time periods to adapt to the facility's needs.

Follow up coaching sessions may be automatically scheduled in the system using various learning and memory based schedules when integrating new movement patterns. Follow up coaching may be scheduled based on real-time data. This provides flexibility to increase the urgency of a coaching session for a worker if their risk levels rise in a short period of time.

In addition to the identification of particular activities based on extraction of orientation and acceleration data from the sensor device 190, additional context may be provided for the data by sensors or communication protocols used to calculate a user's location within a facility or a distance from another object. For example, in an indoor facility, beacons may be distributed, and Wifi or Bluetooth signal strength or triangulation may be used to estimate the position of the invented device inside the facility. Similarly, in an outdoor environment, GPS can be used to estimate location. In some embodiments, distance from a known object may be estimated based on signal strength between the sensor device 190, and a device or beacon at a known location relative to the object.

Information about the worker's location may allow for identifying additional worker activity as well as worker physical activity with increased accuracy. For example, if the platform detects that a worker has entered a region for which he is not authorized, the device may trigger an alert to the worker or the worker's supervisor.

Further, by locating multiple users and pieces of equipment, the platform may detect when a worker comes within a threshold distance of a moving piece of equipment, such as a heavy truck or forklift, and may trigger an alert to the worker.

Further, the wearable device 190 may determine if a worker has collided with a moving vehicle or is otherwise injured by detecting any impact through the accelerometer, evaluating a resting orientation of the worker, and/or using location information to determine the distance to an object in order to determine the cause of an impact. In those cases, the device may vibrate to alert the worker and/or send an SOS to the server 310 and potentially alert emergency responders.

While the worker log is described in terms of detecting and analyzing worker injuries, the log may be used in a variety of different ways. As the wearable device 190 is able to detect and identify certain activities performed by the worker, it can detect unsafe postures, such as high risk bends, twists, and reaches. It may also detect workers jumping off vehicles or even slips, trips, and falls. The wearable device 190 may also detect safe postures, such as squats. Using methods to distinguish different categories of physical activity, as discussed above, allows for the creation of a log which maps all activities of a worker's day (or of some other defined period of time). The log may then be used to map what percentage of time is spent in safe postures, and what percentage of time is spent in unsafe postures. Other activity may be identified as well, such as driving a forklift or other vehicle, taking a break, walking, etc.

In addition to directly identifying injuries, the log may then be used to generate a risk score over time which could then be correlated to injuries. Such a risk score, similar to some embodiments of the cumulative risk metric discussed above, may help an employer understand and predict the likelihood of injury to particular workers or the overall workforce. Such a log, as well as the associated prediction of injury likelihood may In some embodiments, the sensor device 190 may also be used to time stamp when a user comes into work, takes a break, or ends work by confirming the time period for which the user is within a work zone. Accordingly, a device trigger can be used to determine how many hours an employee has worked, and if they are allowed into the premises. Triggers can be based on a variety of activities, such as taking the device 190 out of its dock and returning it, putting the device 190 on and off of a belt, starting to walk after putting the device on, scanning an employee badge, or pressing a button or taking other action on the device 190 once a worker puts it on.

Accordingly, the device 190 measures some trigger event to indicate that a worker is starting use and has started their shift. The system may then integrate the device 190 into the facilities time management system to determine the time periods that workers are in attendance. In some embodiments, when the worker clocks in, a display on the wearable device 190 may change color to indicate attendance. The device may then similarly change color to indicate a break or clocking out.

Further, while a user is at work, location can be used to assist in determining an activity performed, as a user location can be correlated with detected motion in order to label physical activity based on time or location. Further, in determining the particular activity performed, the user location can be used to determine what activities would be expected to be performed in a particular location.

The wearable device 190, together with the activity detection methods described, may provide additional insight into the productivity of workers and/or facility design.

Activity logs for individual workers may be reviewed to evaluate, for example, the number of times a worker performs a specified activity, and how long the activity takes, among other data points. This information may then be mapped and optimized. For example, mapping and breaking down the tasks performed by a warehouse associate who is fulfilling an order will show them picking up an order in a first location in warehouse, walking to a specific shelf location to check inventory, spending three minutes searching for the specific item, walking to a boxing and shipping location, and leaving the box on a pallet for pick-up by a package delivery company. This information may be recorded for several employees, and the warehouse or process could be redesigned in order to optimize the most common activities. This may be by relocating goods or by reassigning tasks based on differences between workers of the system.

In the context of project management and validation, the systems and methods described may be used to confirm that workers have performed required tasks. For example, on a construction site the sensor device 190 could be used to determine what time an electrician clocked in, which floor they spent most time on, an amount of motion and activity measured, how long they spent working in that location, and how that compares to what was planned for the day. Invoices can be generated based on this data, as well as progress reports for specific projects. Further, worker efficiency may be evaluated based on the correlation between an actual log of physical activity generated by the methods described herein using the wearable device 4010 and a user schedule identifying expected activities for the worker.

Productivity metrics may be developed and utilized based on frequency of detection of certain activities. Such data may be analyzed to search for relationships with other detected metrics. For example, productivity can be correlated to changes in dehydration as measured by sweat sensors, such as in the system discussed below in reference to FIG. 4B, or to times of the day, weather, or ambient or body temperature.

FIG. 4A shows a system in which the wearable device 190, described generally as a wearable device 4010, may be implemented. As shown, a worker 4000 may be provided with a wearable device 4010. The wearable device 4010 typically includes multiple communication interfaces, as discussed above. This allows the wearable device 4010 to connect to servers 310 either directly or through a cloud computing interface 4020, in order to upload and receive information, as well as additional sensors 4030, 4040, 4050 on the worker's body which may communicate with the wearable device 4010 and may be provided to keep the worker productive and safe. These additional sensors 4030, 4040, 4050 may be applied directly to the worker's body, as in the case of sensor 4040, or may be integrated into safety equipment, such as sensor 4030, integrated into a harness, and 4050, integrated into a kneepad.

The multiple communication interfaces may provide an ability to communicate data in real time, including warnings and alerts, through the wearable device 4010, using long range communication methods like sub-GHz and cellular radio as well as short range communication methods, such as WiFi and Bluetooth. In some embodiments the wearable device 4010 may further provide a local wired port, such that sensors may be connected using, for example, a USB connection.

The sensors are typically small and use low power communication like Bluetooth Low Energy to send warning messages, and may be, for example, a gas detection sensor. Warning messages may be received at the wearable device 4010 and communicated in real time to the wearable device 4010 in order to trigger an alert, where appropriate. Alternatively, the wearable device 4010 may receive raw data from the gas detection sensor which may then be evaluated at the wearable device 4010, and may trigger an alert when an unacceptable level is detected.

The sensors may be integrated into safety equipment, such as the harness 4060 containing sensor or transmitter 4030. In such an embodiment, the wearable device 4010 may determine if a worker is performing a task or is in a location in which such a harness 4060 is required. If so, the wearable device 4010 may require confirmation that the harness 4060 is present and is securely attached before authorizing a worker 4000 to perform an activity. For example, in order to determine if such a harness 4060 is required, the wearable device 4010 may detect the altitude of the worker, and if the worker is at a high altitude and proper usage of the harness 4060 is not detected, the wearable device 4010 may alert the worker and ground personnel.

In some embodiments, the wearable device 4010 has onboard memory and processing capability, such that the device may save and analyze data to determine if real time feedback to the worker or to an external entity is necessary and, if so, communicate this feedback. Alternatively, or in addition to such on board processing, some portion of the data analytics may be done on cloud servers or local servers upon receipt of the data from the device, as opposed to in real time.

Another potential communication method involves pairing the wearable device 4010 with a gateway residing within the communication range of the device. For example, using long range 400-1000 MHz signals to send the data from the device on a worker to the gateway within one mile radius. The gateway can rely on satellite communication at remote locations to send the data in real time to the external entity. In some implementations, such as on construction sites, a trailer with a communication hub may be provided, and the communication hub may then connect to the individual workers of a system implementing the methods described.

In some embodiments, the additional sensors, such as the wrist sensor 4040 may use the wearable device 4010 as a gateway for relaying information to a server, or as a centralized processing unit. Accordingly, the wrist sensor 4040 may detect information about the worker, such as pulse rate, temperature, and hydration. This information may be detected directly, or it may be derived, such as deriving dehydration by evaluating skin conductance or sweat detection. The wrist sensor 4040 may then send the data to the wearable device 4010 for analysis, and the wearable device may then provide recommendations, such as a recommendation to rest or drink water. Further, as discussed above, the data recorded may be correlated with other data collected in order to, for example, evaluate the effect of dehydration on productivity.

Further, the invention can be employed to ensure compliance with Personal Protective Equipment (PPE) policies, such as confirming that a user is wearing gloves, hard hats, eye glasses, as well as other safety equipment, such as harnesses, in appropriate situations.

As an example of PPE compliance, eye protection glasses can have a low power Bluetooth transmitter monitored by the wearable device 4010. If a worker forgets their eyewear and walks out of range of the transmitter contained therein, the wearable device 4010 can notify the worker.

In some embodiments, PPE may be tied to a location within a warehouse. Accordingly, if a worker is detected to have entered a location that requires hard hats or other equipment and is not wearing such equipment, they may receive a message reminding them or they may not be able to perform their tasks until the equipment is detected.

Similarly, the wearable device 4010 may monitor activities to determine if an activity being performed is authorized for a particular worker 4000 or requires particular safety equipment. As an example, a forklift may have an NFC, RFID, or Bluetooth transmitter. When a worker approaches the forklift, the wearable device 4010 may determine if the worker 4000 is authorized to drive that forklift, and may confirm the proper use of safety equipment, such as a harness. If a worker 4000 is not authorized to perform an activity, the wearable device 4010 may trigger an alert to a manager.

In some embodiments, the wearable device 4010 may function as a key for equipment, such as the forklift, and may transmit an activation signal for the equipment where appropriate. Accordingly, the wearable device 4010 may transmit such a signal only if the user is authorized to use the equipment, and if the user is using all required safety equipment. In this way, the wearable device may change the status of the equipment (on/off, repair mode, maintenance requests, etc.). The wearable device 4010 may function as a key to login and enable or disable access to equipment. The equipment may be enabled only when the wearable device is active and in the vicinity, or only when the wearable device has permission to use the equipment.

In some embodiments, authorization to use the equipment may be based on a risk metric, such as that discussed above. Accordingly, a wearable device 4010 may only be granted access to particular equipment when the device confirms that a user is under a safety threshold, such as below a number of high risk postures (HRPs) for a period of time. Similarly, equipment may be disabled immediately if the worker's wearable device 4010 registers a HRP or a slip or fall. The equipment may also be disabled, or a worker may not be granted access, based on risk of use. For example, someone with high levels of fatigue may not be able to use a particular piece of equipment.

Alternatively, the wearable device 4010 may function as a remote control for machinery with or without active user control. For example, the movement of mobile carts, forklifts, robotic arms, or other industrial equipment may be remotely controlled. Such equipment may also be automatically deactivated when a worker is in the equipment path or within a specified distance. This may be determined based on geofencing technology. Equipment may be activated or the status may be changed remotely, such as shutting down an area and notifying nearby workers due to a safety hazard.

As one form of remote control, the wearable device 4010 may function as a beacon for self-navigating robots to follow the worker around a warehouse or the like without active user control. Similarly, the beacon may be used as a target for the robots, such that they automatically deliver packages to the worker.

FIG. 4B shows an additional system in which the wearable device 190 may be implemented. As shown, the worker 4000 may similarly be provided with a wearable device 4010 which includes multiple communication interfaces. As shown, short range communication interfaces 4100, such as Bluetooth, WiFi, Zigbee, or NFC may be provided to communicate with local devices, machines, or sensors, while long range communication 4110, such as cellular service, ISM band, or a longer range WiFi platform, may be provided in order to allow for communication with a cloud computing platform 4120 or a server 310.

In such a system, the short range communication 4100 allows the wearable device 4010 to communicate with the local environment. For example, a machine 4120 on which the user is working may be equipped with sensors to assist in diagnostics. Accordingly, the status of such machines may be provided to the worker 4000 when the worker approaches that particular machine.

Similarly, the machine 4120 may communicate with the wearable device 4010 in order to assist the various methods described above to identify a particular physical activity in which the worker 4000 is engaged, or in order to allow the wearable device 4010 to determine if any safety equipment should be required for the user.

As another example, in such a system, multiple environmental sensors may be distributed throughout a work environment in order to monitor various environmental data, such as local humidity or temperature, or to detect danger, such as elevated gas levels. Accordingly, the wearable device 4010 may retrieve data from a local environmental sensor when the user is within range of the individual environmental sensors.

Such environmental sensors may be provided with transmitters with minimal communication range in order, for example, to preserve battery life or prevent interference. However, in some embodiments, the information from those environmental sensors may require centralized processing. Accordingly, when the wearable device 4010 is within range of such an environmental sensor and retrieves data from it using the short range communication interface 4100, it may then relay that data to the server 310 using the long range communication interface 4110.

Accordingly, in such a system, the server 310 may be configured to record the environmental data in a database with the identification of the corresponding sensor from which the data was acquired. By maintaining the data from multiple environmental sensors acquired at various times by multiple workers, the system may achieve high resolution data by receiving, for example, humidity data from humidity sensors distributed across a work environment when any of several workers 4000 of the system described walks past such a sensor. This data may then be analyzed and monitored for changes. If, for example, a gas level or pressure level spikes, or data otherwise differs drastically from an expected data point, an alert may distributed to all workers. Similarly, information from sensors in different locations may be monitored, and if adjacent environmental sensors show different environmental data, the sensors may be checked for either localized problems or sensor errors.

Figure 4C:
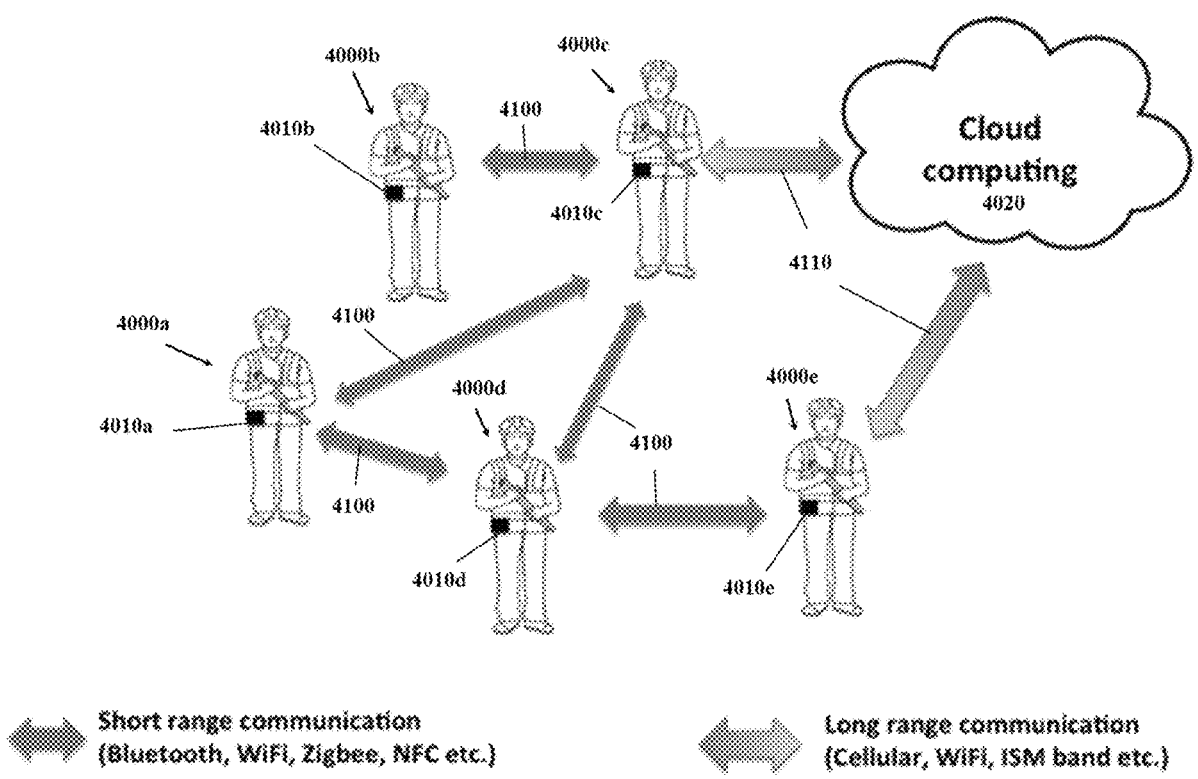

FIG. 4C shows an additional system in which the wearable device 190 may be implemented. As shown, the worker 4000 may similarly be provided with a wearable device 4010 which includes multiple communication interfaces, as in the system shown in FIG. 4B. However, in such an implementation, the short range communication interface 4100 provided may be used by a first worker 4000*a* to communicate with additional workers 4000*b-e* in order to bypass long range communication, or to pass a signal to different workers 4000*c* within range of long range communication 4110 when the first worker 4000*a* is out of such range.

Such a system may be implemented in order to increase the overall range of the system, such that when wearable device 4010*a* of a first worker 4000*a* is out of range of the cloud computing platform and therefore cannot relay information to a server 310, it may instead relay information to a wearable device 4010*c* of a secondary worker 4000*c* which can in turn relay the data to the cloud computing platform 4020. Accordingly, while the system described in reference to FIG. 4B discusses the relaying of data using the long range communication interface 4110 to transmit the data to a server 310, the system could instead relay to other workers 4000*b*.

The system may further be implemented in order to use mesh networking protocols, such as Zigbee, to have wearable devices 4010*a-e* communicate directly with each other. For example, the wearable device 4010*a* of the first worker 4000*a* may detect some risk, such as elevated gas levels. The wearable device 4010*a* may then trigger a warning in nearby wearable devices 4010*b-e*.

A system in which user wearable devices 4010*a-e* may communicate directly with each other may also support direct messaging between workers.

A mesh network may be implemented using beacons and workplace equipment, as discussed herein. Communications may leverage zigbee, Bluetooth Low Energy, Bluetooth 5, or WiFi direct, among other communication protocols. Such mesh networks can provide bidirectional information to the wearable device 4010. For example, it may alert workers in case of an emergency, it can interact with facility systems, and workers can send alerts to other workers, as well as to the facility itself. The mesh network may also serve as a redundant form of communication to insure delivery of messages and link facility equipment to communicate safety issues.

Wearable M2M communications can be used to trigger events or control equipment, as discussed elsewhere herein. A wearable device 4010 can be used to clock in and out of a facility, and can alert a worker when certain equipment provides information. Equipment can know who is near or operating it. Accordingly, the mesh network can authorize permissions for specific workers, and the equipment can record and transmit user information, such as application rates or usage duration or frequency. The wearable device 4010 can also act as an electronic lock out/tag out system.

Figure 5:
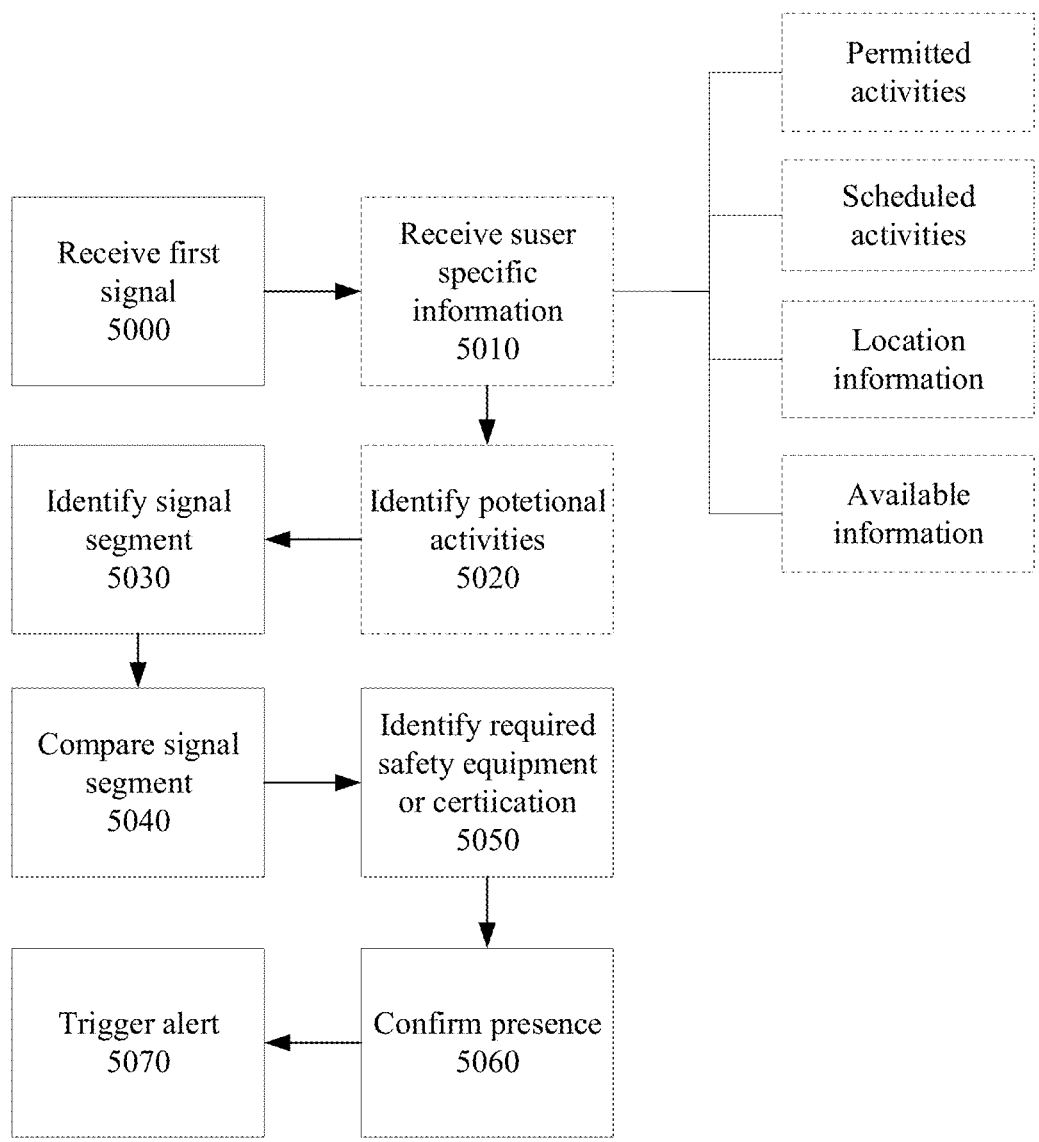
FIG. 5 illustrates a method for enforcing safety rules.

FIG. 5 illustrates a method for enforcing safety rules implemented in the systems shown in FIGS. 4A-C. As shown, the method first receives (5000) a first signal from a worker's wearable device 4010 indicative of physical characteristics of that wearable device over time. In some embodiments, the method may be further provided (5010) with additional information specific to the worker, such as permitted or scheduled activities for that user, or information related to a location. In such embodiments, the method may then identify (5020) based on the additional information a set of physical activities that could be expected to occur either by the particular worker or at the worker's location. For example, if the worker is at a high altitude, or at a loading dock, specific physical activities may be expected. Similarly, the method may receive information related to objects or industrial equipment present at the location. For example, if a worker is determined to be adjacent a forklift, that worker could be expected to drive the forklift.

The method then identifies (5030) in the signal a signal segment corresponding to one of several expected physical activities and compares (5040) that identified signal segment to expected signal segments for each of the expected physical activities. Once a particular physical activity is identified, the method may identify (5050) specific safety equipment or certifications as required for the physical activity and may confirm (5060) that the item of safety equipment or certification is present. This may be implemented, for example, in the system shown in FIG. 4A by providing the safety equipment with a transmitter so that it can communicate with the wearable device 4010. In such an embodiment, the wearable device may confirm the presence of a signal from the safety equipment.

If the presence of the safety equipment cannot be confirmed, the method may trigger an alert (5070) either to the worker or to a supervisor warning that the activity should not proceed until the safety equipment is used. For example, if a worker is at altitude, but cannot be confirmed to be wearing a harness, an alert may be triggered by the method. In some embodiments, the method may prevent further activity by the worker. For example, if the worker is operating equipment without proper safety equipment, such as a worker using or preparing to use a forklift without proper harnessing, the wearable device may transmit a signal to the forklift to turn off, or may prevent the forklift from turning on.

A signal from the safety equipment may, in addition to indicating the presence of the safety equipment, indicate proper implementation of the equipment. For example, a user may be notified if a harness is improperly attached, or if a hard hat is present but not being worn.

In the system shown in FIG. 4B, for example, the wearable device 4010 may be in communication with a piece of industrial equipment that requires activation. In such an embodiment, the wearable device 4010 may contain an activation key to be transmitted to the industrial equipment. In such a system, the activation key may be transmitted only if an item of safety equipment required for the operation of the industrial equipment is confirmed to be present. In such an embodiment, the activation key may be transmitted to the industrial equipment upon receipt of a confirmation signal from the safety equipment.

Further, the method may limit the types of activity it searches for based on proximity to industrial equipment. For example, when a worker 4000 uses a forklift, the method may monitor acceleration and deceleration profiles to determine risk associated with the user's driving. Hard braking or extreme acceleration may be tracked, and the speed of the vehicle may be estimated. Further, any impact can be evaluated.

Figure 6:
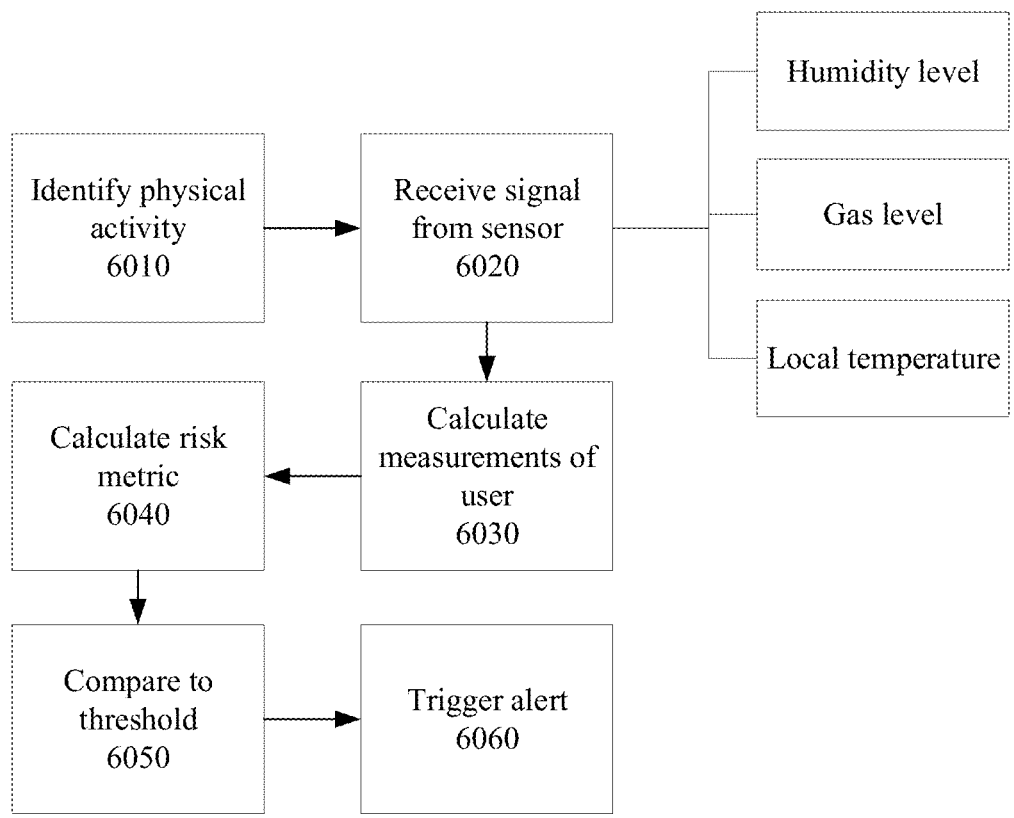
FIG. 6 illustrates a method for triggering a risk alert.

FIG. 6 illustrates a method for triggering a risk alert in the context of the system of FIG. 4B. As shown, a worker 4000 may be provided with a wearable device 4010. Using, for example, portions of the method of FIG. 5, the system may first identify a physical activity (6010) performed by a worker 4000 of the system based on a first signal retrieved from the wearable device 4010. The method may separately receive (6020) a signal from an environmental sensor independent of the wearable device 4010. Such a signal may provide environmental data, such as a humidity level, gas level, or temperature level for the worker's location. The method may then calculate measurements (6030) of the worker 4000 from the first signal for a time period corresponding to a physical activity being evaluated and may then calculate a risk metric (6040) from a risk model incorporating the environmental data received from the environmental sensor, compare (6050) the risk metric calculated to a threshold and trigger (6060) an alert of the risk metric indicates a risk level above a safety threshold.

Incorporating the environmental data into the risk metric may increase the calculated risk in certain scenarios. For example, high humidity may increase worker fatigue, resulting in an increase of risk level associated with a particular activity.

Environmental data may also provide information about the location and status of equipment. For example, a worker may be provided with information about the last known worker of specific equipment, or a date of most recent maintenance on the equipment. Workers may be provided with alerts if moving pieces of equipment are getting too close and should be avoided. Similarly, the system can also track workers of specific machinery, to monitor chain of custody if equipment breaks or to find a most common worker for equipment.

This type of equipment specific data, or metrics related to equipment data can be used to compare the risk metrics, discussed above, with worker activities. This can be used to determine a safe or high risk posture rate to calculate productivity or safety metrics. For example, if equipment indicates that a worker has lifted or placed 1000 boxes, the system may indicate what percentage of such actions were safe and what percentage involved HRPs.

Figures 7, 8:
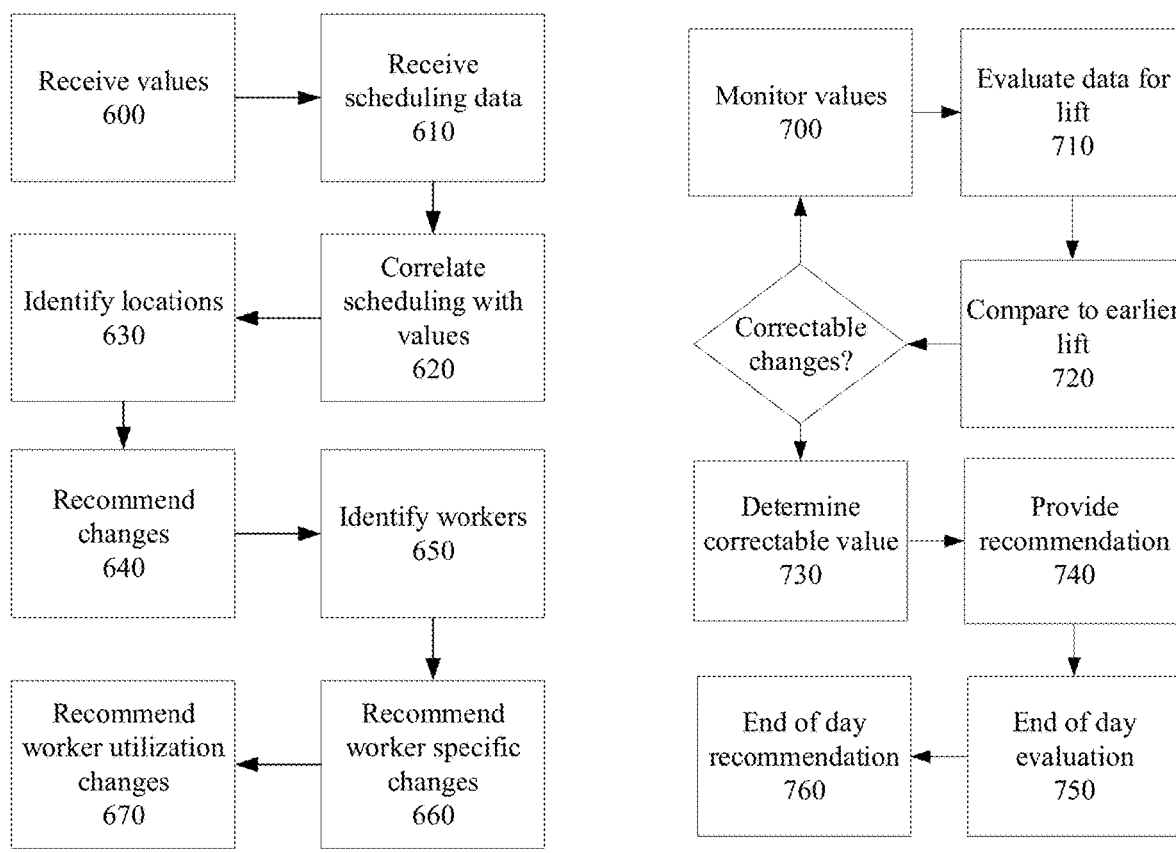
FIG. 7 illustrates a method for generating recommendations.
FIG. 8 illustrates an alternate method for generating recommendations.

FIG. 7 illustrates a method for generating recommendations based on the data and risk model outputs received in the method of FIG. 3. The server first receives (600) values for the risk metric calculated in such a method with respect to individual physical activities for multiple workers.

The server further receives (610) scheduling data for individual workers including information related to the location within a warehouse that each worker is assigned to. This scheduling data typically contains, for each worker, a location at which they would be working at any given time. The server then correlates (620) the scheduling data with the risk metric for individual lifts in order to determine a location for the individual lifting activities associated with the risk metrics calculated.

The server then identifies (630) specific physical locations, in the form of warehouse sector numbers, for example, at which the risk metric illustrates a high risk across multiple workers. The method may then recommend (640) location based changes based on the data underlying the risk metric showing high risk. For example, where the risk metric shows that multiple employees are at increased risk because an object must be lifted from a high location, the platform may recommend lowering a shelf on which objects rest or adding a stool for workers to stand on while lifting. Similarly, if workers consistently rotate their backs excessively while performing a task at a specific location in a warehouse, the platform may recommend adding a conveyor to that sector of the warehouse.

Similarly, the server may identify specific tasks rather than physical locations, that result in increased risks for workers. For example, if the first worker 110 and the second worker 140 both generate increased values of the risk metric when their schedules indicate that they were each performing a specific task. Accordingly, if multiple workers consistently demonstrate increased risk when, for example, unloading trailers, that task may be highlighted as a high risk task, and the platform may recommend a change in the methodology for performing that particular task.

A platform incorporating the method may present this data in a number of ways. For example, it may provide a heat map illustrating metric values.

Rather than incorporating worker schedules, in some embodiments, the sensors 190 may have an additional module for determining worker location by, for example, incorporating a GPS unit or other geolocation components and processes. Alternatively, the sensors may triangulate the location of workers based on proximity to known landmarks, such as beacons.

The server may further identify (650) specific workers with higher average risk metrics than others in specific areas. In such a scenario, the method may recommend (660) changes specific to that worker, such as corrections to the worker's posture, or it may recommend (670) utilizing that worker in a different location in the warehouse where they would not be placed at risk. For example, where a specific worker is shorter than others and therefore shows an increased risk in a specific location, the platform may recommend reassigning that worker to a different region.

Accordingly, if a particular job is categorized as high risk for a particular worker, based on wearable device data and previous history data, the amount of time the worker spends on that task can be optimized. Similarly, if a worker is engaged in a high risk activity, the data can be analyzed in real time to determine if a worker should change takes based on the rate of high risk postures and energy expenditures.

In some embodiments, workers can receive individualized messages at their own devices 4010. This may be based on worker biomechanical data, such as specific advice to focus on reducing twists, for example. Messages may further advise taking breaks as a response to fatigue metrics. Messages can further relate to worker task assignments related to certain stations, machines, or locations. For example, "station number XY12" would allow a worker to confirm which station they are assigned to. Similarly, a machine or task may be assigned to a worker. The worker may then push a button or tap the wearable device to indicate task completion.

Additional messaging features are considered as well. For example, workers may be grouped based on a region within a building or work environment, and messages may be sent to a group and displayed on each worker's wearable device 4010. This could notify workers of region specific information or warnings, or may provide instruction upon entering or leaving the region. The messages could similarly alert workers to emergency procedures, such as triggering a building evacuation.

The device may display additional messages on the screen as well, such as messages related to safety and productivity. These may include reminders to stay hydrated, for example. Messages may relate to locations, and may be triggered when the wearable device passes a specific location. For example, as the worker passes by a prohibited area, a message may indicate the same to the worker.

Further messaging may be provided based on conditional needs of an organization. For example, a group of workers may be summoned to the manager's office using the messaging features. Similarly, messaging can be used to notify workers of dynamic operational needs of an organization, such as for increased output, schedule changes, or logistical changes.

Social motivation and competition may be incorporated into a work environment using the methods described. Accordingly, the wearable device 190 can be used to encourage motivation towards the goal of reduced injury risk and improved productivity in several embodiments. In some embodiments, feedback may be provided to individual workers relating their performance to the performance of others. This may be in the form of a rank on a leaderboard, for example.

In such an embodiment, a worker wearing the device, can access, through the device or through a related platform, an employee ranking or leaderboard which shows the rank of the worker for a specific metric compared to their peers. For example, a ranking of workers may be provided based on the number of high risk lifts they have performed over a given time period. By seeing their rank, a worker may be motivated to improve their performance, especially if combined with incentives, such as a gift card, points etc.

Alternatively, a worker may be provided with a daily target for a specific metric, which can then be shown on the screen of the device. When the worker achieves the goal, the device may provide a notification to the worker or management. For example, a target for a productivity metric, such as number of lifts, or a goal for a safety metric, such as the number of lifts performed with good biomechanical posture may be created within the systems described. Workers may be alerted when they achieve daily goals or are ranked well relative to coworkers. Information displayed to individual workers would be catered to their individual needs based on their biomechanics data.

The platform may further advise on shift changes. In this embodiment, workers who are at increased risk of injury after a certain number of hours of their shift because of fatigue, or other reasons, can be shifted to another task that uses alternate muscles in order to reduce their risk of fatigue induced injuries. In addition, the unloading or loading of a trailer, or other high intensity tasks, can be scheduled to coincide with times of the shift where workers at least fatigued.

FIG. 8 illustrates an alternate method for generating recommendations. As shown in the figure, the server monitors (700) the values of the risk metric determined in the method of FIG. 3A across multiple physical activities for a specific worker. If a specific one of the physical activities performed by the worker demonstrates increased risk as measured by the risk metric, the platform evaluates (710) the data underlying the specific physical activity being evaluated. The platform then compares (720) each of the underlying metrics to the corresponding metrics determined for earlier corresponding physical activities performed by the same worker.

If the underlying metrics differ in a specific identifiable way from earlier lifts, the platform determines (730) if the underlying metrics is correctable by the worker, and if so, provides a recommendation (740) to address the change. For example, where the platform notes that the horizontal distance between the workers back and wrist has changed, or the worker's back angle has shifted, it may recommend correcting the worker's posture. The platform may determine that the value has changed by checking each value underlying the metric for each physical activity against the average value of the corresponding measurement. If there is a significant difference, such as if the value differs by more than a threshold percentage, the platform may recommend a corresponding change.

Further, in some embodiments, if the risk as described by the model is above a threshold, the individual components of the risk models may be analyzed to determine the cause of the underlying risk, and to present recommendations for addressing the high risk level. For example, if the risk metric provides an increased value and the platform determines that the frequency multiplier is abnormally high, recommendations may be provided based on reducing the frequency rates of a specified activity, such as lifts or having more workers perform the job so as to reduce the load on each individual worker.

This recommendation may be provided to a worker as soon as detected by the platform by providing feedback corresponding to the aspect of the worker's posture that should be addressed. For example, where the distance between wrist and back has changed, haptic feedback may be applied to the worker's wrist, while if the back angle has changed, such feedback may be applied to the worker's back.

Additional recommendations may be generated by the platform. For example, depending on the values for the variables underlying the risk metric, the platform may recommend bringing a load closer to the worker by removing any barriers or obstacles between the worker and the load, avoiding lifts beginning near the floor, avoiding lifts over shoulder height, reducing the vertical distance between the origin and the destination of a load, reducing a lifting frequency, or allowing for longer recovery periods between lifts. Further, the platform may recommend improving posture by straightening the worker's back and lifting with his legs or turning feet and stepping to move loads rather than having a worker twist his back.

In addition to recommendations, a platform implementing the method may generate actionable visualizations by summarizing metrics recorded over the course of an evaluation period, or over an extended period of time, by providing charts indicating high risk times of days, weeks, or months, so that specific risks may be identified and addressed. The platform may further identify, for example, a percentage of high risk lifts or total number of high risk lifts performed in a specified period of time.

Such an evaluation may be done in real-time by providing such feedback during a work shift. Alternatively, or in addition, the platform may provide (750) an end of day evaluation. Such an evaluation may, for example, demonstrate worsening posture over the course of the day indicating fatigue. In such a scenario, the platform may provide a recommendation (760) such as a scheduling change or a reorganization of tasks. For example, the platform may recommend lifting heavier objects earlier in a shift.

While the method is described with respect to a risk metric, the method may further be used to monitor productivity across tasks for individual workers. This may be by monitoring, for example, frequency of lifts, or productivity over the course of a shift. For both the methods illustrated in FIGS. 7 and 8, where recommendations are made, the results of those recommendations may be monitored based on the productivity metric as well as the risk metric in order to evaluate whether the recommended change was effective. Accordingly, where a piece of equipment was recommended and implemented in a specific location, the platform may monitor future activity in that location to determine if injury risk has in fact decreased and/or to determine if productivity has in fact increased in that location. This information can be incorporated into future modeling of that particular change.

Metrics relating to productivity of individual workers may be further developed, and productivity based metrics may be utilized to evaluate relationships between fatigue and productivity. Accordingly, the platform may provide estimates of return on investment for individual pieces of equipment that may both reduce injury risk and increase productivity. In some cases, a reduction in injury risk may lower productivity, while a requirement for a worker increasing productivity may increase the risk for that particular worker. The platform described may determine an appropriate balance of increasing a worker's productivity while maintaining the risk metric below a specified threshold.

In some embodiments, fatigue of workers may be evaluated by estimating energy associated with motion of the worker. Fatigue affects risk and is typically incorporated into measurements in the form of lift rate, and in generating an effective weight lifted, as discussed above with respect to step 490. Fatigue may be further evaluated by monitoring average acceleration rates of the wrist and back of the worker over time, including during non-lifting activities, such as inventory checking or manufacturing processes. By detecting reductions in acceleration rates over time, such a method may then identify fatigue and determine potential and kinetic energies expected by a workers body.

The platform described may provide immediate feedback to workers themselves, or it may provide feedback directly to managers, either through on screen notifications at their workstations or through text messages to immediately notify a manager to an increase risk level for an employee. Similarly, the platform may provide rankings for individual workers, or may alert the manager when the workplace as a whole has generated an increased risk profile.

Figure 9:
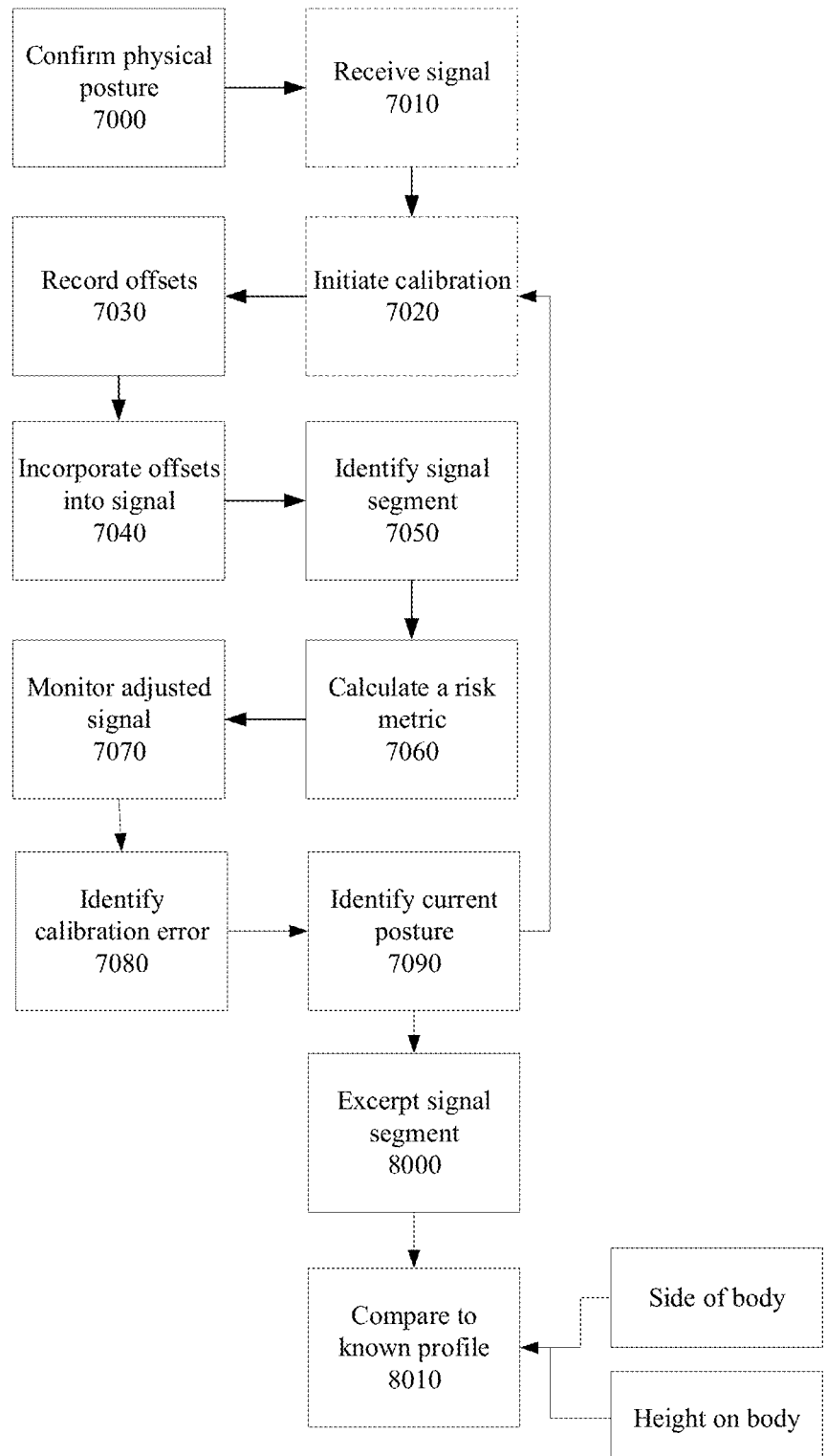
FIG. 9 illustrates a method for calibrating wearable sensors.

FIG. 9 illustrates a method for calibrating wearable sensors 190. Such a method may be implemented using the sensor packaging 2000 shown in FIGS. 2B-2D in order to properly calibrate the sensors 190 prior to beginning the detection of particular activities.

The method initially confirms (7000) that an actual physical posture or movement of a worker wearing the wearable device 4010 corresponds to a known physical posture or movement, captures an initial state of all sensors, and begins to receive (7010), at a processor, a first signal from a wearable device 4010, the signal indicative of physical characteristics of the wearable device 4010 over time. For example, the signal may reflect orientation, height, or acceleration information indicative of the location and movement of the wearable device 4010 over time.

The actual physical posture may be, for example, a standardized standing or sitting position. The confirmation of such posture may be by monitoring a clip 2010 on the wearable device 4010 and proceeding with the method upon the closure of the clip. The closure of the clip 2010 may be detected by a switch integrated into the clip, such as a magnetic field sensor or reed switch. In some embodiments, a worker may be instructed to assume a particular posture, such as standing up straight, and may then confirm that they have assumed the posture by, for example, gesturing or pushing a button confirming the posture assumed posture. In some embodiments, a worker may tap the wearable device 4010, resulting in a spike of acceleration data from the accelerometer 210, in order to indicate that the posture has been assumed. In some embodiments, such confirmation may be a voice command, a gesture, a physical switch, or a proximity sensor.

Alternatively, the method may require the worker to assume one of several known postures and instruct a worker to either sit straight up or stand straight, and the wearable device 4010 may detect which position has been selected and calibrate accordingly.

The method then initiates (7020) a calibration sequence. The calibration sequence correlates the first signal received from the wearable device 4010 with the known physical posture of the device at that time. Accordingly, the calibration sequence includes recording offsets (7030) for the first signal in a memory, the offsets accounting for any difference between an expected first signal and the physical characteristics actually measured in the first signal.

The offsets recorded may include offsets to be applied to raw data from a 3-axis accelerometer 210, gyroscope 220, magnetometer, or altimeter, or to a fusion of data, such as quaternion data.

Once the offsets are recorded, they are incorporated (7040) into an adjusted first signal, and the adjusted first signal is then used to implement the various methods described elsewhere in this disclosure. Accordingly, once the first signal is adjusted, the method identifies, (7050) in the adjusted first signal, a signal segment corresponding to a physical activity, and calculates (7060) a risk metric from a risk model based on the signal segment corresponding to the physical activity, the risk metric being indicative of high risk physical activity.

Figure 10A:
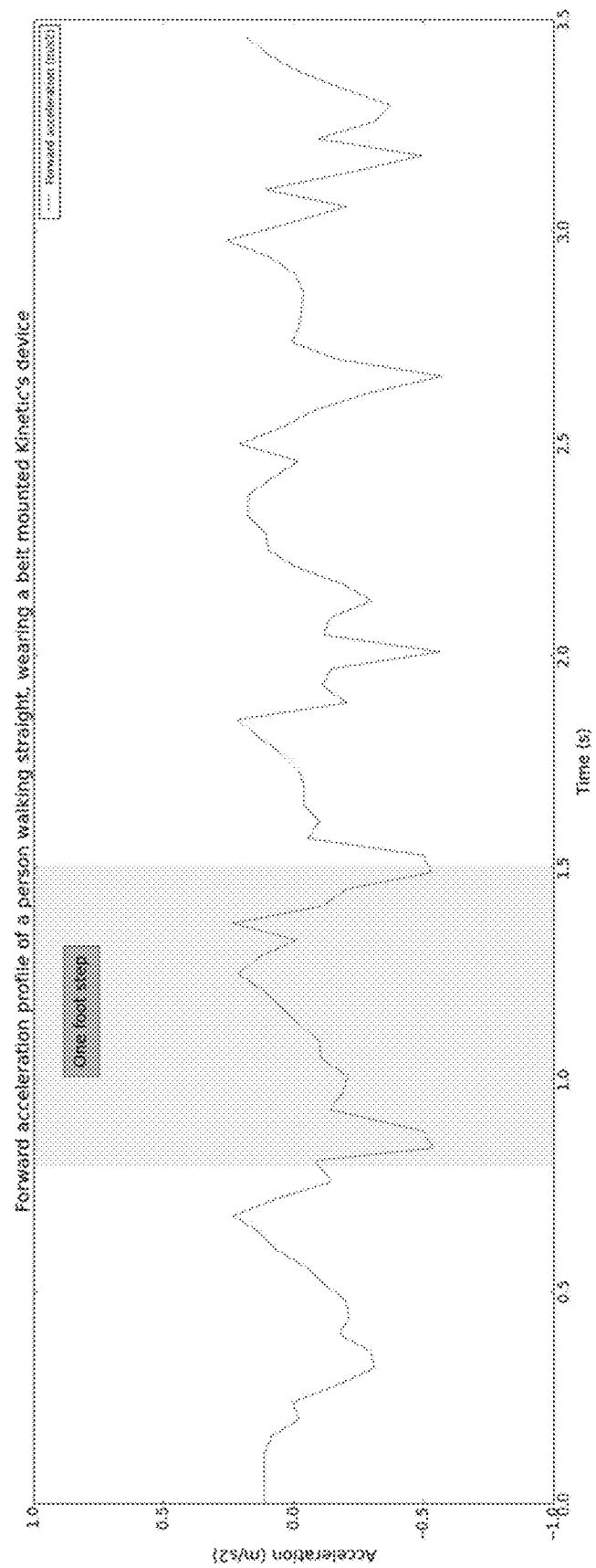
FIGS. 10A-B show acceleration profiles generated by the wearable sensors.
Figure 10B:
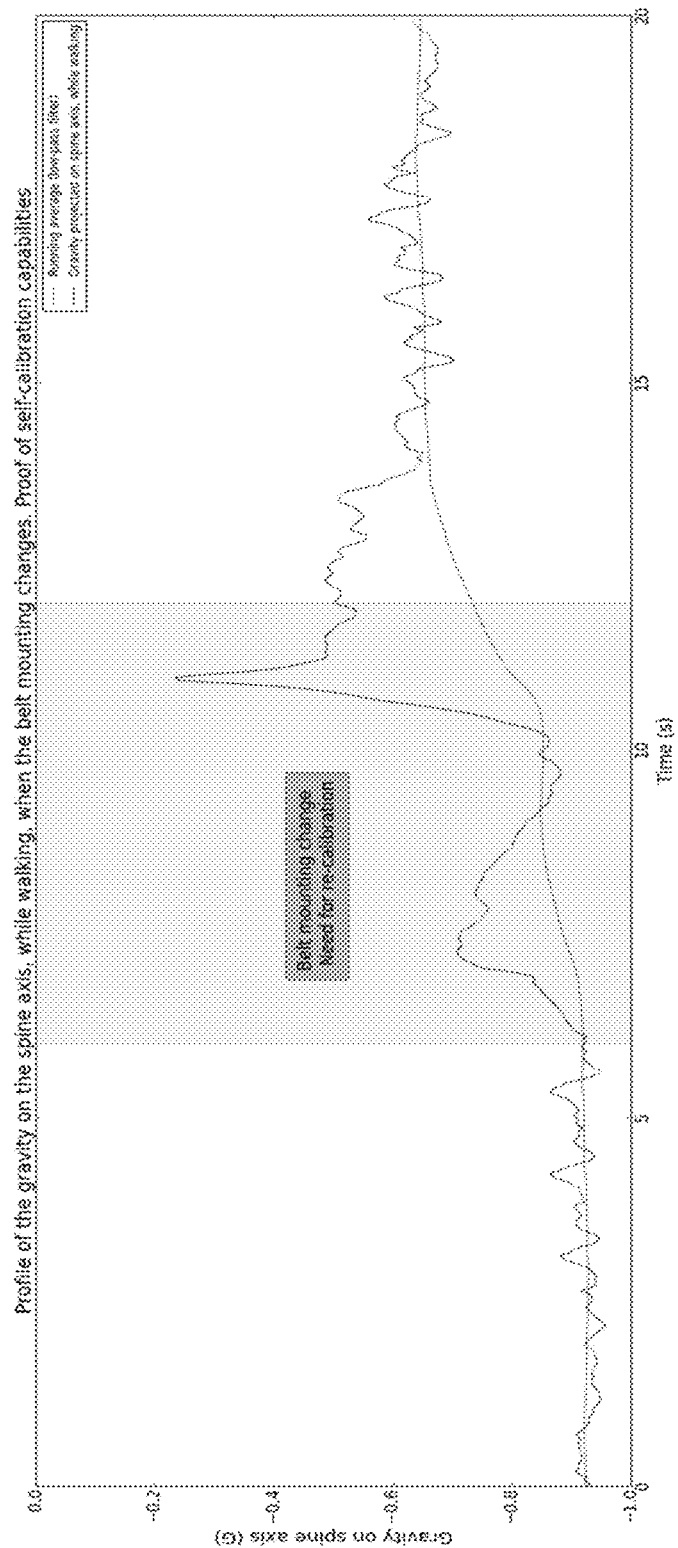

In some embodiments, the method continues to monitor (7070) the adjusted first signal and identifies (7080) a signal segment corresponding to a known category of calibration error. For example, if the wearable device 4010 is knocked and is rotated with respect to the worker's belt line or slides along the worker's belt, the adjusted first signal may provide data indicating a dangerous motion, when the data really indicates a calibration error based on the new positioning of the wearable device. As one example, FIG. 10A shows an acceleration profile corresponding to a user of the wearable device 4010 walking. FIG. 10B shows that acceleration profile modified by a known category of calibration error, where, for example, the wearable device 4010 is knocked out of alignment while the user is walking.

Accordingly, if such a calibration error is detected, the method may identify (7090) the current actual posture or motion of the user by incorporating the calibration error into its evaluation and reinitiate (at 7020) the calibration sequence. In some embodiments, the calibration sequence is reinitiated at regular intervals, regardless of whether a known category of calibration error is detected, in order to maintain proper calibration.

The identification of the current actual posture or motion of the worker (7090) may be, for example, by monitoring the first signal for common known acceleration profiles, such as a worker walking profile shown in FIG. 10A. The method may then implement the calibration sequence while the worker is walking by, for example, averaging the movement of the user to determine the appropriate offsets for the device. In other embodiments, the method may observe the worker walking to confirm that the segment of the first signal is, indeed, indicative of a calibration error and may then initiate (at 7020) the calibration sequence when the worker stops walking, assuming the worker remains upright.

Alternatively, once the system is properly calibrated, the method may monitor a moving average of common known acceleration profiles. In such a case, if the moving average moves dramatically, such as that shown in FIG. 10B, the moving average algorithm may either modify the offsets or compensate the algorithms accordingly. Various statistics other than a moving average may be used as well.

In some embodiments, the calibration method may further determine a wearing position or device location of the wearable device 4010 relative to the worker. To do so, the method may monitor (7090) common known acceleration profiles, such as the profile of a user walking shown in FIG. 8A, and may excerpt a calibration signal segment (8000) corresponding to a known action, such as a single footstep or a set of footsteps. The method may then compare (8010) the calibration signal segment to expected profiles for that known action based on assumptions that the wearable device 4010 is worn in different positions, such as above or below the pelvic bone or on the left or right hip. In some embodiments, the calibration signal segment may, instead, be compared to the expected profiles and variance of the signal relative to the expected profile may be used to identify wearing positions corresponding to known variances.

Figure 11B:
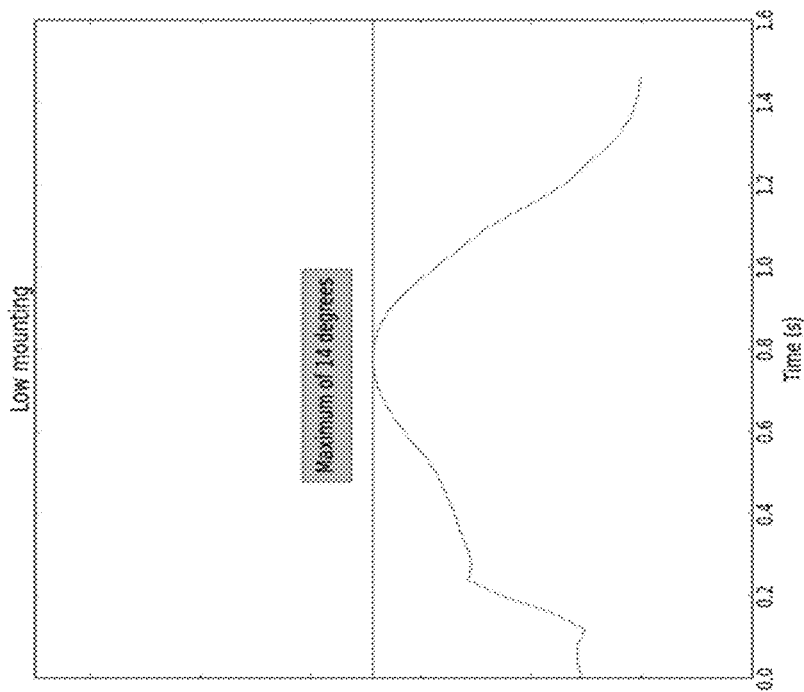
FIGS. 11A-B show rotation profiles generated by the wearable sensors.
Figure 11A:
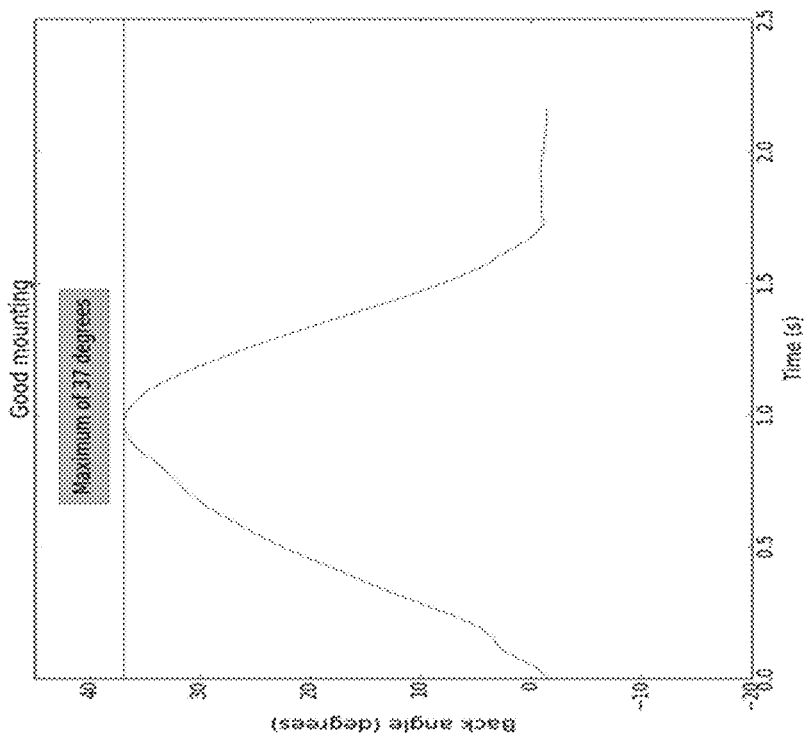

For example, when a worker bends over, the maximum rotation of the wearable device 4010 will vary depending on whether it is worn higher or lower than expected. FIG. 11A, for example, shows the rotation of a wearable device 4010 against time for a worker bending over when the device is properly mounted above a worker's hip. As shown, the worker's back angle is properly measured to achieve a maximum rotation of 37 degrees. In contrast, FIG. 11B shows the rotation of the wearable device 4010 for the same action when the device is mounted lower on the worker's body, showing a maximum rotation of 14 degrees. Accordingly, when the method identifies an improper profile, such as that shown in FIG. 11B, the method may either trigger an alert, instruct the user to correct the mounting position, or it may modify the algorithms or recalibrate the device accordingly.

Accordingly, the devices 4010 are optimized to be located at a specific region of the body, such as wrist or hip. Knowing if the worker has located it correctly is important. Wearing the device too high or too low, as well as too far forward on the waist, should be corrected. Accordingly in some embodiments, a calibration method may be implemented in order to determine if the wearing location of the wearable device 190. In such an embodiment, the method may first determine that an actual physical posture of a worker wearing the wearable device 190 corresponds to a known physical posture, as at 7000. The method then receives the first signal generated from dynamic activity over time (at 7010) and identifies a calibration signal segment (at 7020) corresponding to an expected pattern for calibration activity and identifies a device location relative to the user based on variance between the calibration signal and the expected pattern (at 8010). In such a method, other portions of the calibration method described may be omitted.

Accordingly, the device location is a side of the user's body or a height relative to the user's hips. Alternatively, the device location may be an offset relative to a user's hip indicating that the wearable device 190 is too far forwards or backwards of the user's hip. The method may then alert the user if the device location relative to the user does not correspond to an expected device location, so that the user may adjust the device location accordingly.

Figure 12B:
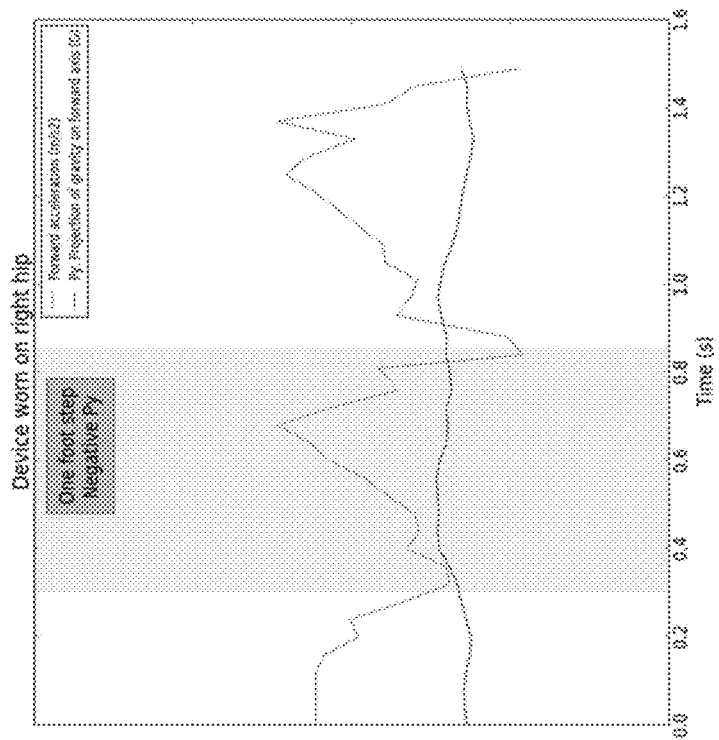
FIGS. 12A-B show acceleration profiles generated by the wearable sensors.
Figure 12A:
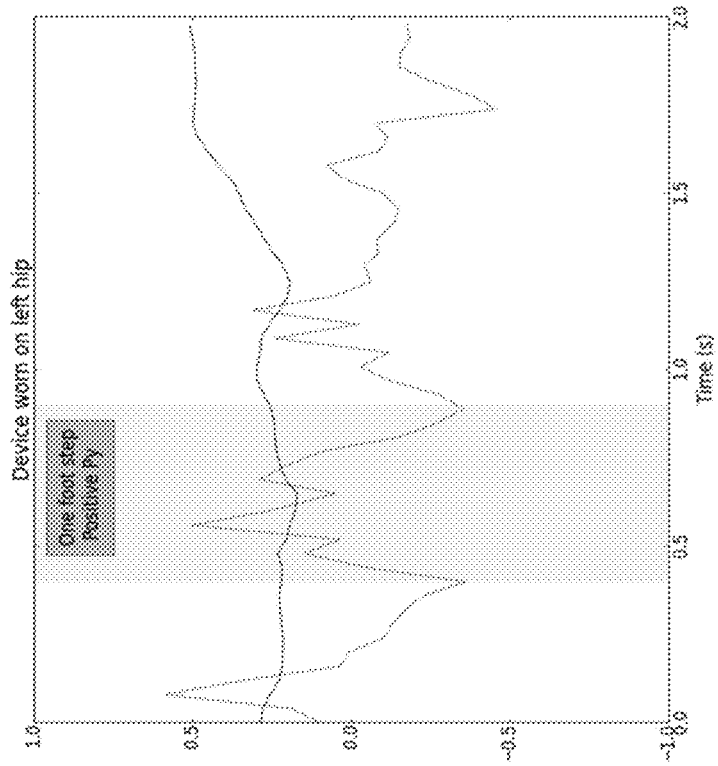

Similarly, an acceleration profile for a known activity will vary depending on wearing position of the wearable device (4010). For example, when a worker is walking, the resulting profile will be different if the worker wears the device on his left hip, as shown in FIG. 12A, than if the worker wears the device on his right hip, as shown in FIG. 12B.

In order to increase the accuracy of the calibration method, a worker may be instructed to perform a known action. For example, a worker may be instructed to bend their back with or without bending their knees in order to determine the mounting height of the wearable device 190. The worker may also be asked to twist their back in order to determine the maximum rotation of the wearable device 4010 in that context.

Many features of the methods and systems described are enhanced by associating each wearable device 190 with a specific worker. The proper association during ensures accurate and consistent evaluation of risk metrics, and further ensures that measurements are associated with the correct worker.

In some embodiments, the device may be assigned to a particular worker through a software web interface, using the serial number of the device, the device name, label, or alias, for example. This information is then stored on a web server and communicated to the device. In order to confirm the association, the device may, for example, display the worker's name and a unique company label. Every day before work starts, the worker picks up their associated device showing his or her name and the unique label number.

In some embodiments, the identification of a particular worker may be based on details within the calibration signal segment discussed above. For example, when a worker initiates the calibration process, the method may track a user walking for a few steps and then analyze the user's gait in order to identify the particular user.

In some embodiments, the wearable devices 190 each have RFID readers to read the worker's badge or entry card and associate themselves to that worker. This may be done on a daily basis, such that each day a worker may pick up one of several available wearable devices 190 and associate that device with their own profile. Alternatively, the association may be manually created by a worker entering their name, employee ID or other unique identifying feature at a worker interface, so the device can associate the data to that specific worker. In some embodiments, this association may allow the worker to use the wearable device 190 as a key to authorize access to particular locations within a facility or specific equipment.

In some embodiments, the data and metrics collected and computed by the systems and methods provided can be combined with other available data, both individual to the worker as well as aggregated across the worker, job type, facility, company, or industry. Typical data collection studies might involve:

Identifying industries and jobs involved with musculoskeletal injury risk;

Examining a specified company's injuries records; and

Collecting worker motion sensor data by means of the invented device.

Once these three steps are completed, a study operator could assess current state of the art ergonomic models with respect to their predictive power and limitations while designing dynamic, sensor-based, prediction models.

Most currently used ergonomic models rely on static data points to analyze motion, are based on data collected for only a few days, if not hours, per employee, and per job type, and focus on a very specific activity and do not encompass tasks' true complexity. By using the wearable device 190 described, continuous sensor measurements over longer time periods and across different industries and job types, as well as more granular worker-specific data (such as past injuries, days off work, incident rates, behavior observation, age, gender, and medication taken), correlations between specific repetitive motions and injury factors may be examined and more accurate and precise predictive models may be developed.

The results of such studies may be used to increase the predictability of past data, and may increase the quality of, for example, actuarial evaluations of workers for the purpose of insurance rates. Separately, data may be used to reorganize workplaces for increased safety and efficiency and various safety requirements may be associated with tasks based on particular injury risks uncovered in the data. In some embodiments, worker s may volunteer to be monitored using the wearable device 4010 in exchange for a reduction in their own insurance rate, and the data acquired may be used to more granularly adjust the rate or penalize or reward the worker.

Figure 13:
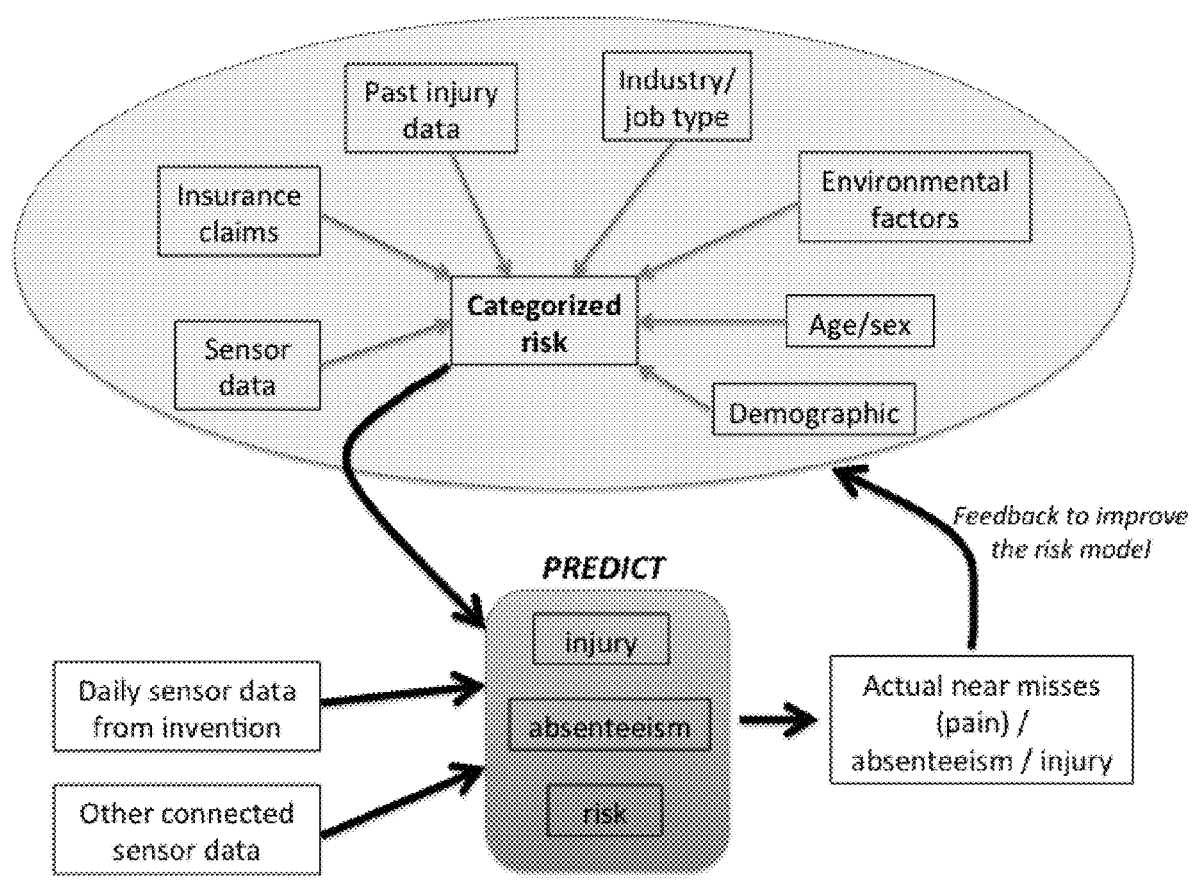
FIG. 13 shows a model for using the methods provided for evaluating risks.

Any model based on the dynamic data described may then generate data that feeds back into the model. As shown in FIG. 13, various categorized risks associate with a worker, including risks based on the sensor data generated and evaluated using the methods described, may be used to predict injury, absenteeism, and other risk. Over time, the model may then be informed of actual injuries, etc., which may then refine the model.

Figure 14:
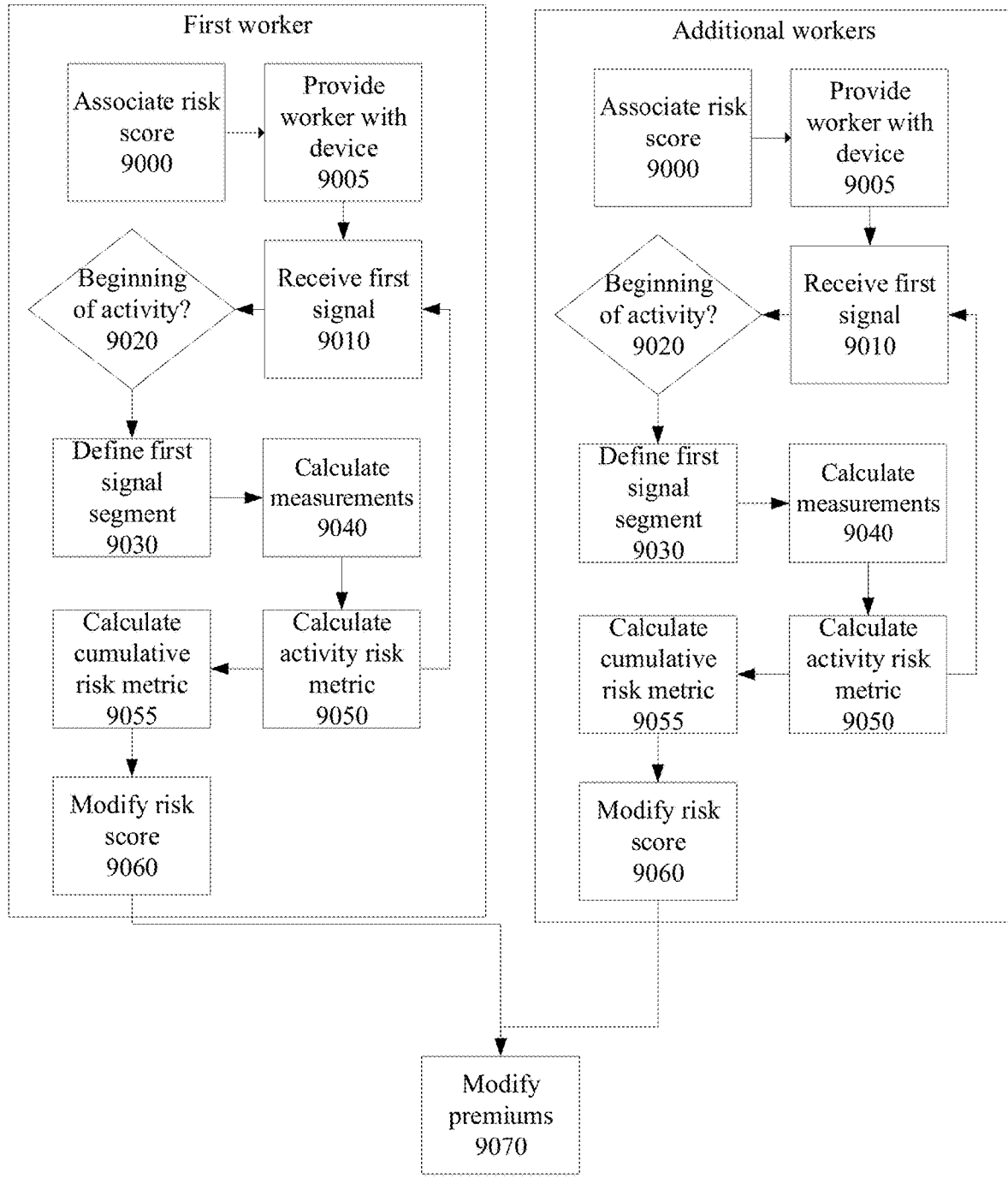
FIG. 14 is a flowchart illustrating a method for adjusting insurance based on worker safety.

FIG. 14 is a flowchart illustrating a method for adjusting insurance based on worker safety. Typically, insurance policies for workers compensation are based on industry expectations for losses for a particular category of worker, historical losses for a client, and several other factors. Accordingly, risk metrics tied to particular workers or groups of workers would be valuable in more precisely assigning insurance risk in the industry.

The method provided initially associates a risk score (9000) with each worker of a group of workers. While the method is described with respect to one worker of the group of workers, each worker in the group would typically be provided (9005) with a wearable device 190 for use in the method, and the method would modify the risk score associated with each worker. Typically, the risk score is a predictive metric for predicting whether an individual or a group has a high probability of incurring an injury.

Accordingly, a first signal is received (9010) from a wearable device 4010 worn by the first worker and generated by dynamic activity of the wearable device over time. An initiation time for a first physical activity of a first category of physical activity performed by the first worker is then identified (9020) in the first signal, and a first signal segment is defined (9030) in the first signal, the first signal segment corresponding to the time period in which the first physical activity is performed. In some embodiments, the first signal segment is extracted from the first signal, while in others, the first signal segment is used directly as part of the first signal. As discussed above, the time window for the first signal segment may be defined based on an expected end time for the first physical activity, or it may be determined based on details in the first signal.

Measurements of the first worker are calculated (9040) for a time period during the first physical activity. Such measurements are derived from and calculated based on data in the first signal segment.

The measurements are then used to calculate (9050) an activity risk metric from a risk model based on the measurements of the wearer for the time period during the first physical activity, wherein the risk metric is indicative of a risk level of the execution of the physical activity by the first worker.

The identification of an initiation time and calculations described above are then repeated to identify a plurality of additional physical activities of the first category of physical activity.

Once risk metrics are calculated and associated with a set of physical activities, such risk metrics are used to modify the risk score of the first worker (9060). Accordingly, if the activity risk metrics indicate that the first workers performance of the set of physical activities was high risk, then the risk score for the first worker may be increased. Similarly, if the activity risk metrics indicate that the first worker successfully minimized the risk associated with his actions, the risk score for the first worker may be reduced. While the risk score is discussed in terms of a high risk score corresponding to a high risk worker, the alternative may be possible as well.

The risk score for the first worker may then be used to modify insurance premiums (9070) for a policy covering that worker. Further, as discussed above, the method would typically be applied to a group of workers. Accordingly, each worker may be provided with a corresponding risk score, which may be modified based on that worker's respective activity risk metrics. The risk scores for the workers in the group may then be incorporated into actuarial tables for the group such that insurance premiums may be calculated or adjusted for the group.

In addition to the activity risk metric (at 9050) and the cumulative risk metric (at 9055), the method may generate a collective risk metric for the group of workers based on the risk scores associated with the individual workers of the group of workers. In such an embodiment, the insurance premium may be calculated based on the collective risk metric.

In some embodiments, a cumulative risk metric may be calculated (9055) for each worker based on multiple physical activities, the cumulative risk metric being indicative of a risk level from the activities over time, and may be used to modify the risk score. Potential metrics for the cumulative risk metric are discussed above. In such an embodiment, the risk score for each worker of the group of workers may be modified based on the cumulative risk score for the corresponding worker.

Further, the method may further comprise generating a penalty assessed against the worker upon the calculation of a risk metric if the risk metric indicates a high risk posture performed by the worker.

The risk score may be modified over time based on data collected by the system. Accordingly, the risk score may be based on correlating motions or features derived from the motions, by way of the activity risk metric, with injuries by workers performing the work. This may be by machine learning algorithms or other statistical methods. Such risk score may leverage the NIOSH and MARRAS models, discussed above, as MARRAS has methods for predicting whether a group has a high probability of incurring an injury compared to a low probability group.

While the method is described generally in terms of a group of workers, a similar method can be used to price a premium for a single worker, whether or not that worker is part of a group. Further, in addition to a worker's particular risk score, the price of an insurance premium can be further based on risk associated with a task or set of tasks performed by the worker. For example, the method may record the full set of tasks performed by a worker over time, and each such task may have a baseline risk level. The combination of such risk levels can be used to generate a baseline insurance premium utilized in calculating the worker's premium.

Using such methods, and by correlating geometric and population features with probability of injury, an estimate of the frequency and severity of claims can be made.

If factors implemented at a facility reduce the probability of injuries to an individual or group that would affect the expected cost of injuries at that site. Such actions could then be rewarded by insurance providers by reducing the cost of a premium or providing a discount on a future premium payment.

Modifications of premium prices may then be made by updating injury rates based on the risk scores calculated by this method. The modification can be done in real time or after a period of time.

While the discussion of premium prices is in terms of group rates for a group of workers, the method may similarly be applied to a single worker, where a risk score for the worker is used to calculate or adjust a premium for that worker.

In some embodiments, the risk associated with performance of activities by workers can be used to adjust payments or assign bonuses to workers. Accordingly, the wearable device can be used to monitor an employee's postures while engaged in manual labor, and to collect data based on the type of motions made, and the quantity and frequency of motions. The data may then be compared to industry quotas or other comparable individuals and then used to affect variable compensation or job assignments.

Figure 15:
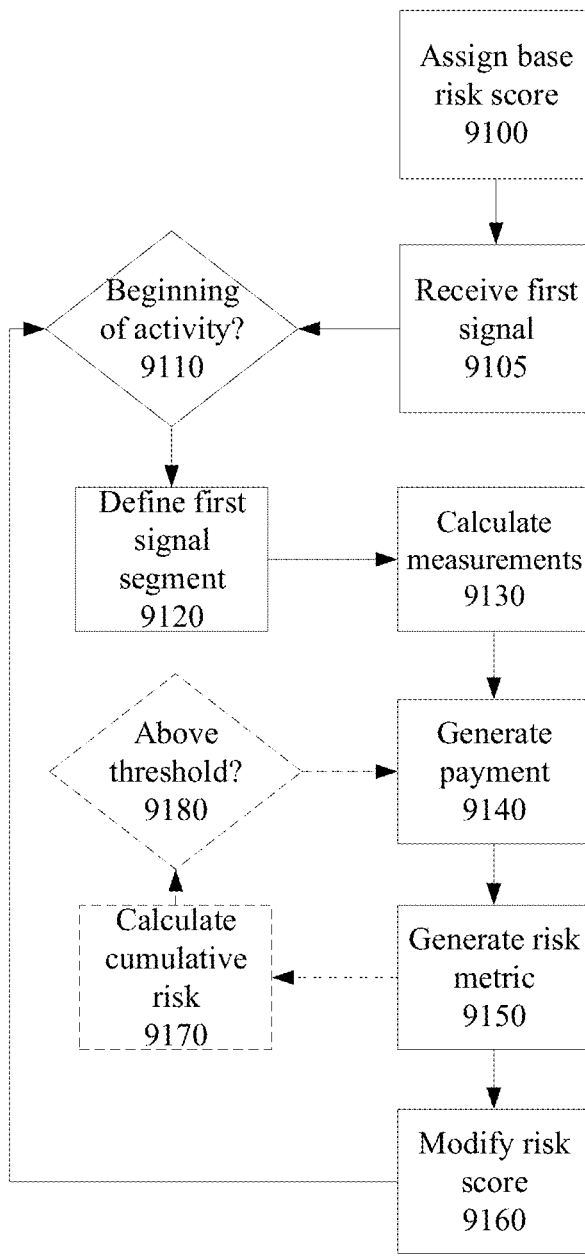
FIG. 15 is a flowchart illustrating a method for incentivizing safe activities by workers.

In one embodiment, the method is for incentivizing risk reduction during physical activities, as shown in FIG. 15, and each worker is assigned a wearable device, such as those discussed above. Each worker may be assigned a base risk score (9100) at the beginning of a shift, or at the beginning of a longer period of time over which the method is implemented. The risk score is used to calculate a rate of payment for the worker. In some embodiments, a plurality of risk scores may be associated with a worker, such that each risk score is associated with a different category of physical activity to be performed by the worker. For example, a first risk score may be associated with lifting actions, while a second risk score may be associated with pushing actions or equipment operation. The method then first receives a first signal (9105) from the wearable device generated from dynamic activity of the wearable device over time. The method then identifies an initiation time (9110) for a first physical activity of a first category of physical activity performed by the worker wearing the wearable device.

The identification of an initiation time (at 9110) can take a variety of forms. In some embodiments, the identification is by identifying a signature in the first signal itself. In other embodiments, the worker may indicate that they are initiating a physical activity. For example, a worker may scan a code on a box prior to lifting or otherwise manipulating the box. Alternatively, the identification may be by a server in communication with the wearable device, and the first category of physical activity may be identified based on a schedule associated with the worker and stored on the server.

Once the initiation time is identified (at 9110), a first signal segment in the first signal may be defined (at 9120), the first signal segment corresponding to the portion of the first signal associated with the timing of the first physical activity. Measurements of the worker are then calculated (at 9130) for a time period following the initiation time corresponding to the first physical activity from the first signal segment.

After a physical activity is performed by the worker, a payment is generated (9140) and provided to the worker based on a calculated rate associated with the first category of physical activity. The calculated rate is based on both the category of physical activity performed and the risk score associated with worker for that particular category of physical activity. As noted above, the risk score is specific to the category of physical activity. Accordingly, when a user performs a lift, for example, they may identify the initiation of the lift by scanning a box to be lifted and then perform the lift. After performing the lift, the worker will be assigned a payment calculated based on the fact that the activity was a lift and the workers personal risk score associated with lifting.

Micropayments per task are already common practice as many employers pay per case lifted or scanned, as opposed to by the hour. The device may display metrics to users, such as productivity metrics (i.e., cases lifted) or payment accrued, as well as performance metrics (i.e., cases lifted per hour) and goals (i.e., target cases per hour).

An activity risk metric is then generated (9150) from a risk model based on the measurements of the wearer for the time period during the physical activity, the activity risk metric being indicative of a risk level of the execution of the physical activity by the wearer. The activity risk metric may be any of the metrics discussed above that quantify the risk of a specified physical activity.

After the activity risk metric is generated (at 9150), the metric may be used to modify the risk score (at 9160) associated with the worker and the first category of physical activity. In this way, the risk score may be adjusted to reflect the risk associated with the particular worker performing the particular type of task. If the activity risk metric reflects a low risk performance of the physical activity by the worker, the risk score may be modified such that a larger payment is generated (at 9140) for future activities. Similarly, if the activity risk metric reflects a high risk performance of the physical activity, the risk score may be modified such that future payments are reduced.

Once the risk score is modified (at 9160), the method is repeated, such that an initiation time for another physical activity is detected (at 9110), measurements are calculated (at 9130), payments are generated (at 9140), and another activity risk metric is defined (at 9150) to identify and score a plurality of additional physical activities of the first category of physical activity.

Although the discussion herein provides for generating payment prior to analyzing a physical activity being performed, in some embodiments, for each physical activity performed, the payment is generated (at 9140) based on the risk score at the time of the activity. In some embodiments, the activity risk metric may be calculated and the risk score modified before generating payment for any particular physical activity.

In embodiments where each worker has a plurality of risk scores, each associated with different categories of physical activities, the modification of the risk score associated with one category would not affect the risk score of a different category. Accordingly, if a worker has good posture for lifts, for example, they may get increased payments for such lifts regardless of their performance of other activities, such as driving.

Typically, each worker will have a distinct set of risk scores for various physical activities. In some embodiments, insurance premiums may be modified based on a complete set of risk scores associated with a grouping of workers.

In some embodiments, in addition to activity risk metrics associated with each worker (at 9150), the method may use either the risk metric or the underlying measurements or signal segments to calculate a cumulative risk metric (9170) indicative of a risk level from multiple physical activities over time. In such an embodiment, the worker may have an associated cumulative risk threshold, such that when the cumulative risk metric is above the threshold, they are at an increased risk generally. In such an embodiment, prior to generating payment (at 9140), the method may determine if the cumulative risk metric is above the threshold (9180). If the cumulative risk metric is above the threshold, a cumulative modification may be applied to the payment, such that payment is reduced. The cumulative modification would be removed from the payment if the cumulative risk metric is brought back below the threshold, such that the payment is increased.

Similarly, in some embodiments, the cumulative risk metric may be calculated across multiple physical activities over time and a bonus payment may be applied to a user if the cumulative metric stays below the cumulative risk threshold for a defined period of time.

In some embodiments, a worker's overall wages could be comprised of fractional payments made for completing tasks and events in the industrial workplace, such as the quantity of boxes lifted or sorted or the number of deliveries made. Specific tasks and biomechanics events may be valued different based on difficulty and economic value to the employer, or by the quality of work done. Such worker payments may be automated and use a programmable contract designed by the employer, and that contract may use fiat currency or blockchain currency to automatically provide payments to workers instantly or after a set period.

In some embodiments, worker job and task assignments would be automatically determined based on productivity data, allowing for live and automatic adjustments to job instructions that could be communicated back to workers via messaging to wearable devices or other equipment. Accordingly, worker messaging could communicate to workers to switch tasks to a new task more suited to their biomechanics, or more urgent based on operational needs.

The productivity and safety data generated by the system and method described may be used to automate worker promotions and company reporting structure. Workers with higher productivity or who are more skillful or safer may be automatically promoted to tasks requiring higher skills or more responsibility.

In addition to modifying payment levels to workers, the data can be used otherwise increase productivity and morale using gamification methods. For example, the device may have a screen where information can be shown. A measure of productivity may be presented on the screen so that the worker can see their productivity level. For example, a measure of productivity could be a number of tasks performed, such as a number of items picked, a number of orders fulfilled, or a number of lifts performed, etc. That measure can be automatically detected by the device, as discussed above, or it may be obtained from a server or otherwise retrieved from a workplace management system.

Further, a goal can be set and shown to indicate to the worker a desired level of the productivity metric. The goal can be based on a unit of time, for example per day or per hour. By displaying productivity in real-time, and being able to compare it to a goal, workers can see how they are performing and can modify their performance accordingly.

In addition, a competitive rank can be displayed on the screen, showing how the worker is performing compared to their peers in the same job or in the same facility or company. In some embodiments, workers can be ranked by number or rate of safe postures, and may be given a bonus based on such rank. Where workers are ranked, a large on site display may be provided to display ranks, provide leaderboards, highlight specific workers, etc.

Accordingly, the device display may present a number of metrics, such as numbers of safe and risky postures, safety performance against goals, steps, calorie estimation, and competitive data, such as rank in a competition, data by teams, and the like. The data may be shared with other workers by email, website, a companion app, social media, or the like. In some embodiments, custom content may be automatically shared with workers based on worker data, such as personalized training videos, safety or productivity improvement tips, praise, reward notifications, and the like. Such sharing may be on the wearable device display, by email, by SMS, or by internet.

The goal assigned to the worker can be static, that is does not change over time. For example the goal of taking 10,000 steps per day to stay healthy.

Alternatively, the goal can also be dynamic, that is, it changes over time, or based on the progress made by the wearer. For example, a goal can be updated if a worker exceeds it for 3 days in a row. That goal could become higher, to challenge the worker to increase that metric. Or if the goal refers to a metric which is desired to be minimized, like the number of high-risk postures, it could be reduced as workers reduce their daily score or metric as it related to high-risk postures.

Goals can also be changed based on interaction by the user—for example if a worker presses the button on the wearable to view their data frequently or is wearing their device frequently, it could be judged that they are engaged and the goal can be modified accordingly.

Further, if workers are showing signs of fatigue, or if incidents of high risk postures are increasing, or when a specific time of day is approaching, such that the worker typically performs higher risk activities, the productivity goals may be reduced.

Figure 16:
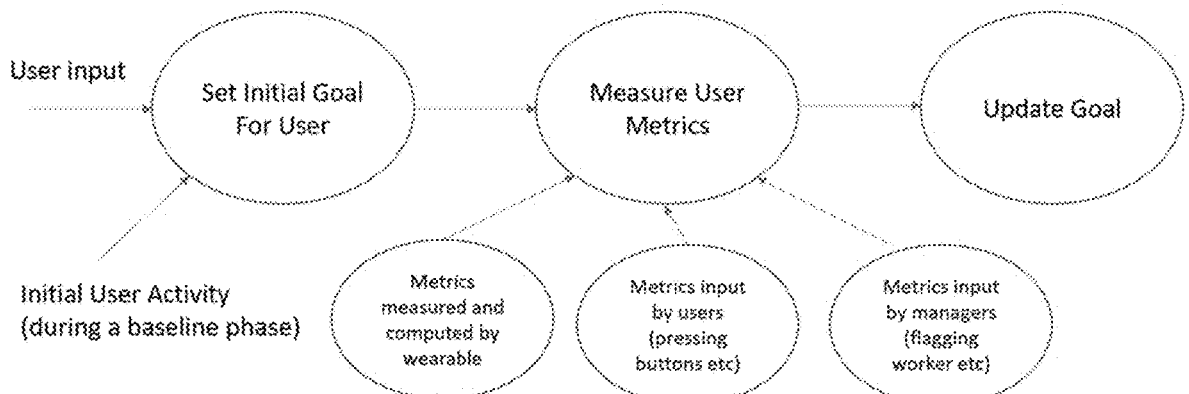
FIG. 16 is a chart illustrating the setting of goals for workers.

Examples of strategies for dynamic updating of goals are shown in FIG. 16.

All the above information can also be sent to a separate system, for example a warehouse management system or a computer system in the workplace and displayed on the screen. For example the performance and goal of workers can be sent to a separate computer and displayed on a screen for workers to see.

Wearable devices referenced throughout this disclosure are used to monitor worker postures and other high-risk motions and to provide workers with immediate feedback to correct the posture or high-risk motion. The wearable devices may also be used to collect data to determine the risk of injury over time. In order to assess such risks and provide feedback, the wearable device must be associated with the worker wearing the device for processing.

Generally, a worker beginning his shift must pick a wearable device already assigned to him, or must follow a procedure to assign a new wearable device to himself. Accordingly, in some embodiments, the device may be assigned to the worker and the worker may then be instructed as to which device to select. In other embodiments, the device may be assigned to the worker immediately before the worker taking the device. In other embodiments, the device may automatically detect which worker it is associated with.

Accordingly, a system for assigning a wearable device to a worker may comprise multiple wearable devices to be assigned to multiple worker. In such a case, the devices may be provided with docking locations, and each docking location may be associated with an identity of the wearable device located at the docking location.

Each docking location may then have an indicator associated with it, such that the indicator identifies the assigned identity for the one of the plurality of wearable devices docked at the corresponding docking location.

Accordingly, in a situation where a worker has an assigned device, and needs to know where to find it among many other devices, each device may be located in accordance with some organizational scheme, and each docking location may thereby identify the wearable device docked at that location. In such an embodiment, devices may be, for example, located in color coded kiosks or carts. Each device is then located at specific charging well, or docking locations.

The device may then be uniquely located within the organizational scheme. For example, the device may have a color and a number, with the color identifying a charging bank or kiosk, and the number identifying a specific docking location within that kiosk. A worker may then be instructed to take the wearable device from a specified location within the organizational scheme.

Figure 17A:
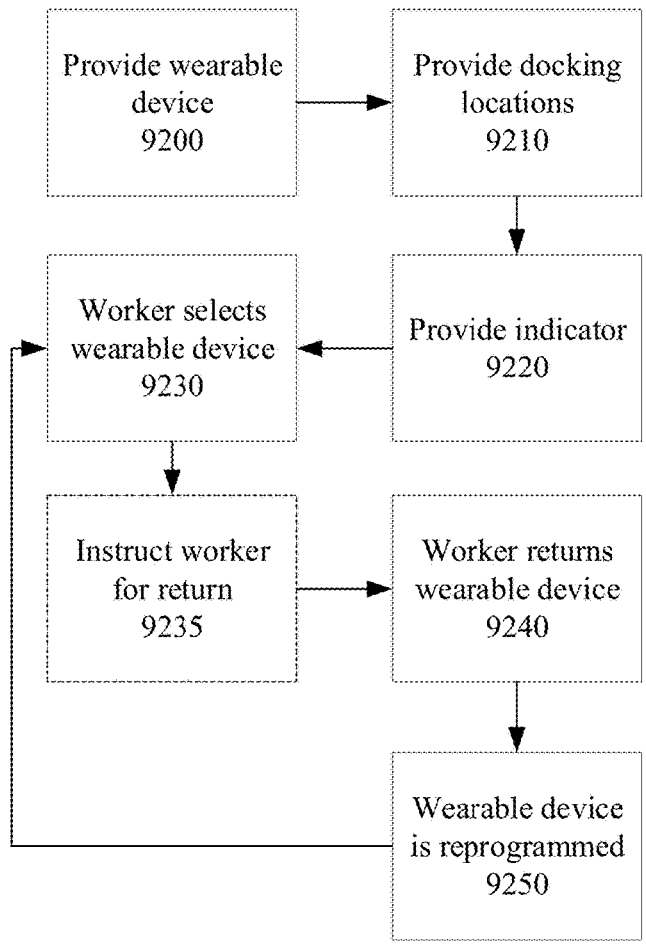
FIG. 17A is a flowchart illustrating a method for assigning a device to a worker.

In order to implement such a system, as shown in FIG. 17A, a work environment is first provided with a plurality of wearable devices (9200) to be assigned to a plurality of workers. The environment is then provided with a plurality of docking locations (9210) for docking the wearable devices, and each docking location is provided with an indicator (9220), where the indicator identifies an assigned identity for the wearable device docked at the corresponding docking location. In some embodiments, the assigned identity may be a particular worker or user to whom the associated wearable device is assigned.

A worker utilizing the system may then be assigned wearable device containing a specified indicator, and may then take the wearable device from the corresponding docking location (9230). In some embodiments, the assigned identity is a scannable code or a readable code, such that when the worker selects a wearable device from a docking location, they can scan the scannable code with a secondary device or enter the code into a device, such as a smartphone or a standalone scanner, thereby assigning the wearable device to himself. In some embodiments, the worker is permanently assigned a wearable device docking location, and the location may be identified on a workers badge or sticker.

The worker may then utilize the wearable device over the course of the day in accordance with the any of the other methods discussed herein. Upon the conclusion of a work day, the worker may then deposit the wearable device at a docking location (9240), where the docking location is not necessarily the same location that he initially took the wearable device from.

Accordingly, where the wearable device is returned to a docking location other than the docking location it has been previously mapped to, the wearable device is reprogrammed (9250) to correspond to the identify identified by the corresponding indicator at the new docking location. In such a way, it is prepared for a worker who may take the wearable device (at 9230) in a following work session.

In some embodiments, a worker may be expected to return the wearable device to the originally identified location, so that the worker uses the same device on consecutive days. In such an embodiment, the identity of the wearable device may be displayed on a screen of the device to help the user remember where to place the device.

Alternatively, the worker may be directed by an indicator, such as an on screen display from the wearable device, to place the device at a specified drop off location (9235). In this way, the worker may be instructed to return the device to a docking location selected by the system from a set of unoccupied docking locations.

In some embodiments, rather than the indicator being associated with a docking location, it may be associated with a particular device. Accordingly, the device may have a permanently assigned label, or a machine readable indicator code may be presented on a display for the device. A worker may then select any wearable device from a set of wearable devices at docking locations. The worker may then scan the machine readable code from the device or display. This may be by way of a bar code scanner or QR code scanner on a tablet or smartphone or other portable device. Alternatively, it may be by way of an RFID tag, a Bluetooth connection, an NFC connection, or another form of digital handshake or coding using either the portable device or the worker's badge. If the tablet or smartphone is not already associated with the worker, the worker may then select their name or otherwise enter their identity at the tablet or smartphone. Alternatively, a worker may scan their worker badge at the portable device. The system may then assign the worker to the device, and the worker can begin work. At the end of the day, the device is returned to any location on the dock. If not wirelessly connected to a server, the device may upload data at the docking location. The indicator may then be reset for the following day, if necessary.

Where a worker uses their badge to associate a wearable device with themselves, the ID must be a human readable or machine readable passive or active ID. The ID can be included in a workers employee access badge, phone, wallet, clothing, or the like. In such an embodiment, a worker association with a wearable device could be recorded at a server and in an appropriate database. This may be by way of the wearable device itself, or it may be by way of a kiosk associated with a docking location capable of reading the ID on the device as well as the employee ID. Data integrity in a large workplace is important, since data can be associated with any one of hundreds or thousands of workers.

In some embodiments, the wearable device detects some element of the worker, such as an RFID or Bluetooth based ID, automatically once the worker takes the wearable device. For example, when the worker wearing the device walks through a door which uses proximity technology to detect the employee through their badge or phone or the like as well as the wearable device, and thereby associates the device and worker. Similarly, the wearable device may automatically pair itself with the worker's smartphone or other portable device using Bluetooth or NFC, thereby associating itself with the worker.

Figure 17B:
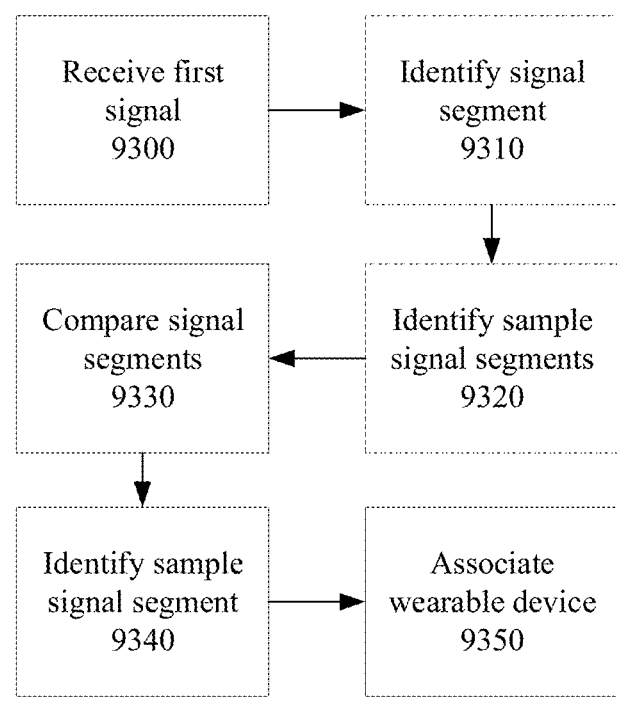
FIG. 17B is a flowchart illustrating a method for assigning a device to a worker.

An alternative method for assigning a wearable device to a worker is shown in FIG. 17B. As shown, the method may first receive, at a processor, a first signal from the wearable device (9300). The method may then identify, in the first signal, a user specific signal segment (9310) corresponding to a performance of a known physical activity. For example, the method may identify a user walking, such that the signal signature associated with the walk may be uniquely associated with a specific worker.

The method may then identify a plurality of sample signal segments (9320) corresponding to the known physical activity, with each of the sample signal segments corresponding to a performance of the known physical activity by a different user. Each of the sample signal segments is there compared (9330) to the user specific signal segment.

The method then identifies (9340) a first sample signal segment corresponding to the user specific signal segment, the first sample signal segment corresponding to the performance of the known physical activity by the worker. In this way, the method identifies a particular user that the user specific signal segment corresponds to. Once identified, the method then associates (9350) the wearable device with the worker.

As noted above, the known physical activity may be the worker walking. Accordingly, the sample signal segments may correspond to users having distinct gaits, such that the user specific signal segment is identified based on a unique gait signature for that worker.

In some embodiments, a database may be created during an initial setup phase to generate the sample signal segments for all workers using the system and method.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" and like terms encompass all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention. Furthermore, the foregoing describes the invention in terms of embodiments foreseen by the inventor for which an enabling description was available, notwithstanding that insubstantial modifications of the invention, not presently foreseen, may nonetheless represent equivalents thereto.

What is claimed is:

1. A computer-based method for calibrating a wearable device comprising:
    determining that an actual physical posture or physical activity of a user wearing the wearable device corresponds to a known physical posture or physical activity;
    receiving, at a processor, a first signal from the wearable device generated from an ongoing dynamic activity of the wearable device over time;
    identifying, in the first signal, a calibration signal segment corresponding to an expected pattern for a calibration activity; and
    identifying a device location relative to the user based on a variance between the calibration signal segment and the expected pattern,
    wherein determining that the physical posture or physical activity of the user wearing the wearable device corresponds to the known physical posture or physical activity comprises recording an indication by the user that the user is in a predetermined physical posture.

2. The computer-based method of claim 1, wherein the device location is a left or ride side of the user's body or a position above or below the user's hips.

3. The computer-based method of claim 1, wherein the device location is an offset relative to the user's hip indicating that the device is forwards or backwards from the user's hip.

4. The computer-based method of claim 1, further comprising alerting the user if the device location relative to the user does not correspond to an expected device location relative to the user.

5. The computer-based method of claim 1, wherein the calibration activity is walking.

6. The computer-based method of claim 1, wherein the indication by the user is tapping the device or pressing a button on the device.

7. The computer-based method of claim 1, wherein the indication by the user is the performance of the predetermined physical activity.

8. The computer-based method of claim 1, wherein the device location is one of the user's chest, torso, or neck.

9. The computer-based method of claim 1, wherein upon identifying the device location, the method alerts the user to indicate a result of the identification.

10. The computer-based method of claim 1, wherein the indication by the user is the fixation of the wearable device to the user.

11. The computer-based method of claim 1, wherein the indication by the user is the closure of a clip for fixing the wearable device to the user.

12. The computer-based method of claim 1 further comprising:
identifying, in the first signal or in the adjusted first signal, a signal segment corresponding to a known category of calibration error or device orientation error, and initiating a recalibration sequence, wherein the known category of calibration error or device orientation error is identified based on measuring the orientation of the device with respect to gravity or the earth's magnetic field.

13. A computer-based method for calibrating a wearable device comprising:
determining that an actual physical posture or physical activity of a user wearing the wearable device corresponds to a known physical posture or physical activity;
receiving, at a processor, a first signal from the wearable device generated from an ongoing dynamic activity of the wearable device over time;
initiating a calibration sequence, the calibration sequence including recording, at a memory, offsets in the first signal relative to an expected value of the first signal corresponding to the known physical posture;
incorporating the offsets into an adjusted first signal;
identifying, in a portion of the adjusted first signal following the calibration window, a signal segment corresponding to a physical activity; and
identifying the physical activity from a plurality of potential physical activities based on the signal segment,
wherein determining that the actual physical posture or physical activity of the user wearing the wearable device corresponds to the known physical posture or physical activity comprises recording an indication by the user that the user is in a predetermined physical posture.

14. The computer-based method of claim 13, wherein the indication by the user is tapping the device or pressing a button on the device.

15. The computer-based method of claim 13, wherein the indication by the user is the performance of the predetermined physical activity.

16. The computer-based method of claim 13, wherein the indication by the user is the fixation of the wearable device to the user.

17. The computer-based method of claim 13, wherein the indication by the user is by way of a capacitive surface of the wearable device or an associated clip.

18. The computer-based method of claim 13, wherein upon completion of the calibration sequence, the method alerts the user to indicate a result of the calibration sequence.

19. The computer-based method of claim 18, wherein the alert to the user is an instruction to correct a mounting position of the wearable device.

20. The computer-based method of claim 13, further comprising:
identifying, in the first signal or in the adjusted first signal, a signal segment corresponding to a known category of calibration error or device orientation error; and
initiating the calibration sequence,
wherein the known category of calibration error or device orientation error is identified based on measuring the orientation of the device with respect to gravity or the earth's magnetic field.

21. The computer-based method of claim 13, wherein the indication by the user is the closure of a clip for fixing the wearable device to the user.

22. A computer-based method for calibrating a wearable device comprising:
determining that an actual physical posture or physical activity of a user wearing the wearable device corresponds to a known physical posture or physical activity;
receiving, at a processor, a first signal from the wearable device generated from an ongoing dynamic activity of the wearable device over time;
identifying, in the first signal, a calibration signal segment corresponding to an expected pattern for a calibration activity; and
identifying a device location relative to the user based on a variance between the calibration signal segment and the expected pattern,
wherein determining that the actual physical posture or physical activity of the user wearing the wearable device corresponds to the known physical posture or physical activity comprises instructing the user to conform to an initial posture and indicate the assumption of that initial posture, wherein the indication is the fixation of the wearable device to the user or the closure of a clip for fixing the wearable device to the user.

23. A computer-based method for calibrating a wearable device comprising:
determining that an actual physical posture or physical activity of a user wearing the wearable device corresponds to a known physical posture or physical activity;
receiving, at a processor, a first signal from the wearable device generated from an ongoing dynamic activity of the wearable device over time;
identifying, in the first signal, a signal segment corresponding to a known category of calibration error or device orientation error, wherein the known category of calibration error or device orientation error is identified based on measuring the orientation of the device with respect to gravity or the earth's magnetic field;
initiating a calibration sequence, the calibration sequence including recording, at a memory, offsets in the first signal relative to an expected value of the first signal corresponding to the known physical posture;
incorporating the offsets into an adjusted first signal;
identifying, in a portion of the adjusted first signal following the calibration window, a signal segment corresponding to a physical activity; and
identifying the physical activity from a plurality of potential physical activities based on the signal segment.

24. A computer-based method for calibrating a wearable device comprising:
- determining that an actual physical posture or physical activity of a user wearing the wearable device corresponds to a known physical posture or physical activity;
- receiving, at a processor, a first signal from the wearable device generated from an ongoing dynamic activity of the wearable device over time;
- initiating a calibration sequence, the calibration sequence including recording, at a memory, offsets in the first signal relative to an expected value of the first signal corresponding to the known physical posture;
- incorporating the offsets into an adjusted first signal;
- identifying, in a portion of the adjusted first signal following the calibration window, a signal segment corresponding to a physical activity; and
- identifying the physical activity from a plurality of potential physical activities based on the signal segment,
- wherein determining that the actual physical posture or physical activity of the user wearing the wearable device corresponds to the known physical posture or physical activity comprises instructing the user to conform to an initial posture and indicate the assumption of that initial posture, wherein the indication is the fixation of the wearable device to the user or the closure of a clip for fixing the wearable device to the user.

* * * * *